(12) United States Patent
Power

(10) Patent No.: US 12,268,590 B1
(45) Date of Patent: Apr. 8, 2025

(54) BRANCHED GRAFT ASSEMBLY METHOD IN VIVO

(71) Applicant: W. L. Gore & Associates, Inc., Newark, DE (US)

(72) Inventor: Adam Howard Power, London (CA)

(73) Assignee: W. L. Gore & Associates, Inc., Newark, DE (US)

( * ) Notice: Subject to any disclaimer, the term of this patent is extended or adjusted under 35 U.S.C. 154(b) by 249 days.

(21) Appl. No.: 17/968,234

(22) Filed: Oct. 18, 2022

Related U.S. Application Data

(60) Continuation of application No. 16/686,657, filed on Nov. 18, 2019, now Pat. No. 11,504,222, which is a division of application No. 15/441,202, filed on Feb. 23, 2017, now Pat. No. 10,512,533.

(60) Provisional application No. 62/298,530, filed on Feb. 23, 2016.

(51) Int. Cl.
*A61F 2/06* (2013.01)
*A61F 2/07* (2013.01)
*A61F 2/95* (2013.01)
*A61F 2/954* (2013.01)

(52) U.S. Cl.
CPC ............... *A61F 2/06* (2013.01); *A61F 2/07* (2013.01); *A61F 2/954* (2013.01); *A61F 2002/061* (2013.01); *A61F 2002/068* (2013.01); *A61F 2002/9534* (2013.01)

(58) Field of Classification Search
CPC .... A61F 2/06; A61F 2/064; A61F 2/07; A61F 2/856; A61F 2/95; A61F 2/954; A61F 2/962; A61F 2002/061; A61F 2002/065; A61F 2002/067; A61F 2002/068; A61F 2002/9511; A61F 2002/9534; A61F 2002/9665; A61F 2220/0075; A61B 2017/1107

See application file for complete search history.

(56) References Cited

U.S. PATENT DOCUMENTS

| | | | |
|---|---|---|---|
| 2,943,153 | A | 6/1960 | Herbert et al. |
| 5,938,696 | A | 8/1999 | Goicoechea et al. |
| 6,102,938 | A | 8/2000 | Evans et al. |

(Continued)

FOREIGN PATENT DOCUMENTS

| | | |
|---|---|---|
| EP | 0806917 B1 | 11/1997 |
| EP | 0915685 A1 | 5/1999 |

(Continued)

*Primary Examiner* — Robert A Lynch

(57) ABSTRACT

A branched graft method includes securing a first end of a branch graft into a first conduit and subsequently moving the second end into a second conduit. The first conduit may be a branch vessel, such as a renal artery and the second conduit may be a main graft that extends over an aortic aneurysm. The branch graft may be deployed starting at an offset distance from the first end, thereby preventing the deployed portion from insertion into the first conduit and predetermining the insertion length into the target vessel. The first end may then be deployed to secure the first end to the first conduit. A branch graft may be a self-expanding stent graft having one or more ripcords, and/or a serpentine ripcord that enables non-linear deployment of the branch graft, or deployment that does not progress from one end to the opposing end.

12 Claims, 28 Drawing Sheets

(56) References Cited

U.S. PATENT DOCUMENTS

| | | | |
|---|---|---|---|
| 6,315,792 B1* | 11/2001 | Armstrong | A61F 2/856 66/81 |
| 6,334,867 B1 | 1/2002 | Anson | |
| 6,458,152 B1 | 10/2002 | Khosravi et al. | |
| 6,676,694 B1 | 1/2004 | Weiss | |
| 6,852,116 B2 | 2/2005 | Leonhardt et al. | |
| 7,220,274 B1 | 5/2007 | Quinn | |
| 7,955,374 B2 | 6/2011 | Erickson et al. | |
| 8,118,862 B2 | 2/2012 | Saeed | |
| 8,182,524 B2 | 5/2012 | Spiridigliozzi et al. | |
| 8,343,204 B2 | 1/2013 | Osborne | |
| 8,353,947 B2 | 1/2013 | Thistle et al. | |
| 8,434,393 B2 | 5/2013 | Adams | |
| 8,672,989 B2 | 3/2014 | Schreck et al. | |
| 8,702,791 B2 | 4/2014 | Kelly | |
| 8,709,068 B2 | 4/2014 | Shalev et al. | |
| 8,821,567 B2 | 9/2014 | Saeed | |
| 8,945,200 B1 | 2/2015 | Eblacas et al. | |
| 9,149,382 B2 | 10/2015 | Greenberg et al. | |
| 9,283,068 B2 | 3/2016 | Kelly | |
| 9,358,142 B2 | 6/2016 | Johnson | |
| 9,452,069 B2 | 9/2016 | Argentine et al. | |
| 9,610,182 B2 | 4/2017 | Douglas | |
| 10,512,533 B1* | 12/2019 | Power | A61F 2/07 |
| 11,504,222 B1* | 11/2022 | Power | A61F 2/06 |
| 2002/0120327 A1 | 8/2002 | Cox et al. | |
| 2002/0128703 A1 | 9/2002 | Ravenscroft | |
| 2003/0120333 A1 | 6/2003 | Ouriel et al. | |
| 2003/0191518 A1 | 10/2003 | Spiridigliozzi et al. | |
| 2003/0195614 A1 | 10/2003 | Ryan et al. | |
| 2004/0199241 A1 | 10/2004 | Gravett et al. | |
| 2004/0225349 A1 | 11/2004 | Thistle et al. | |
| 2005/0149173 A1 | 7/2005 | Hunter et al. | |
| 2005/0177222 A1 | 8/2005 | Mead | |
| 2005/0273154 A1 | 12/2005 | Colone | |
| 2007/0162109 A1 | 7/2007 | Davila et al. | |
| 2008/0255656 A1* | 10/2008 | Saeed | A61F 2/954 623/1.12 |
| 2008/0275536 A1 | 11/2008 | Zarins et al. | |
| 2009/0216315 A1 | 8/2009 | Schreck et al. | |
| 2009/0259298 A1* | 10/2009 | Mayberry | A61F 2/954 623/1.35 |
| 2009/0264821 A1* | 10/2009 | Mafi | A61B 17/11 606/214 |
| 2009/0299454 A1* | 12/2009 | Jennings | A61F 2/954 623/1.11 |
| 2011/0022153 A1 | 1/2011 | Schreck et al. | |
| 2011/0130828 A1* | 6/2011 | Sithian | A61F 2/07 623/1.23 |
| 2011/0251664 A1 | 10/2011 | Acosta De Acevedo | |
| 2011/0288622 A1 | 11/2011 | Chan et al. | |
| 2012/0130478 A1 | 5/2012 | Shaw | |
| 2014/0172064 A1 | 6/2014 | Kelly | |
| 2014/0180379 A1 | 6/2014 | Fleming | |
| 2014/0194970 A1 | 7/2014 | Chobotov | |
| 2014/0277353 A1 | 9/2014 | Hartley | |
| 2014/0364934 A1 | 12/2014 | Hartley et al. | |
| 2015/0057737 A1 | 2/2015 | Ondersma et al. | |
| 2015/0148889 A1 | 5/2015 | Angel et al. | |
| 2015/0173923 A1 | 6/2015 | Mayberry et al. | |
| 2015/0313737 A1 | 11/2015 | Tippett et al. | |
| 2015/0366688 A1 | 12/2015 | Schreck et al. | |
| 2016/0022411 A1 | 1/2016 | Greenberg et al. | |
| 2016/0067067 A1 | 3/2016 | Roselli | |
| 2016/0158043 A1 | 6/2016 | Ehnes et al. | |
| 2016/0184115 A1 | 6/2016 | Ondersma et al. | |
| 2016/0287376 A1 | 10/2016 | Kelly | |
| 2016/0324626 A1 | 11/2016 | Kelly | |
| 2016/0324670 A1 | 11/2016 | Yamaguchi | |

FOREIGN PATENT DOCUMENTS

| | | |
|---|---|---|
| EP | 0918496 B1 | 6/2000 |
| EP | 1087729 A1 | 4/2001 |
| EP | 1489995 A1 | 12/2004 |
| EP | 1530448 A1 | 5/2005 |
| EP | 1572034 A2 | 9/2005 |
| EP | 1581270 A2 | 10/2005 |
| EP | 1622543 A1 | 2/2006 |
| EP | 1689457 A2 | 8/2006 |
| EP | 1696828 A1 | 9/2006 |
| EP | 2008623 A1 | 12/2008 |
| EP | 2142142 A2 | 1/2010 |
| EP | 2152197 A1 | 2/2010 |
| EP | 2349085 A1 | 8/2011 |
| EP | 2445444 A2 | 5/2012 |
| EP | 2453836 A1 | 5/2012 |
| EP | 2459121 A1 | 6/2012 |
| EP | 2549959 A2 | 1/2013 |
| EP | 2563271 A1 | 3/2013 |
| EP | 2640311 A2 | 9/2013 |
| EP | 2777605 A1 | 9/2014 |
| EP | 2837362 A1 | 2/2015 |
| EP | 2875796 A2 | 5/2015 |
| EP | 3031425 A1 | 6/2016 |
| WO | 99/65419 A1 | 12/1999 |
| WO | 2003/084440 A1 | 10/2003 |
| WO | 03/10354 A1 | 12/2003 |
| WO | 2004/047885 A2 | 6/2004 |
| WO | 2004/060424 A2 | 7/2004 |
| WO | 2004/100835 A1 | 11/2004 |
| WO | 2005/058202 A1 | 6/2005 |
| WO | 2008/107885 A2 | 9/2008 |
| WO | 2008/130848 A1 | 10/2008 |
| WO | 2010/024879 A1 | 3/2010 |
| WO | 2010/150208 A2 | 12/2010 |
| WO | 2011/007354 A1 | 1/2011 |
| WO | 2011/012147 A1 | 2/2011 |
| WO | 2011/117736 A2 | 9/2011 |
| WO | 2011/136931 A1 | 11/2011 |
| WO | 2012/067823 A2 | 5/2012 |
| WO | 2014/107748 A2 | 7/2014 |
| WO | 2014/110254 A1 | 7/2014 |
| WO | 2014/149531 A1 | 9/2014 |
| WO | 2016/090112 A1 | 6/2016 |

* cited by examiner

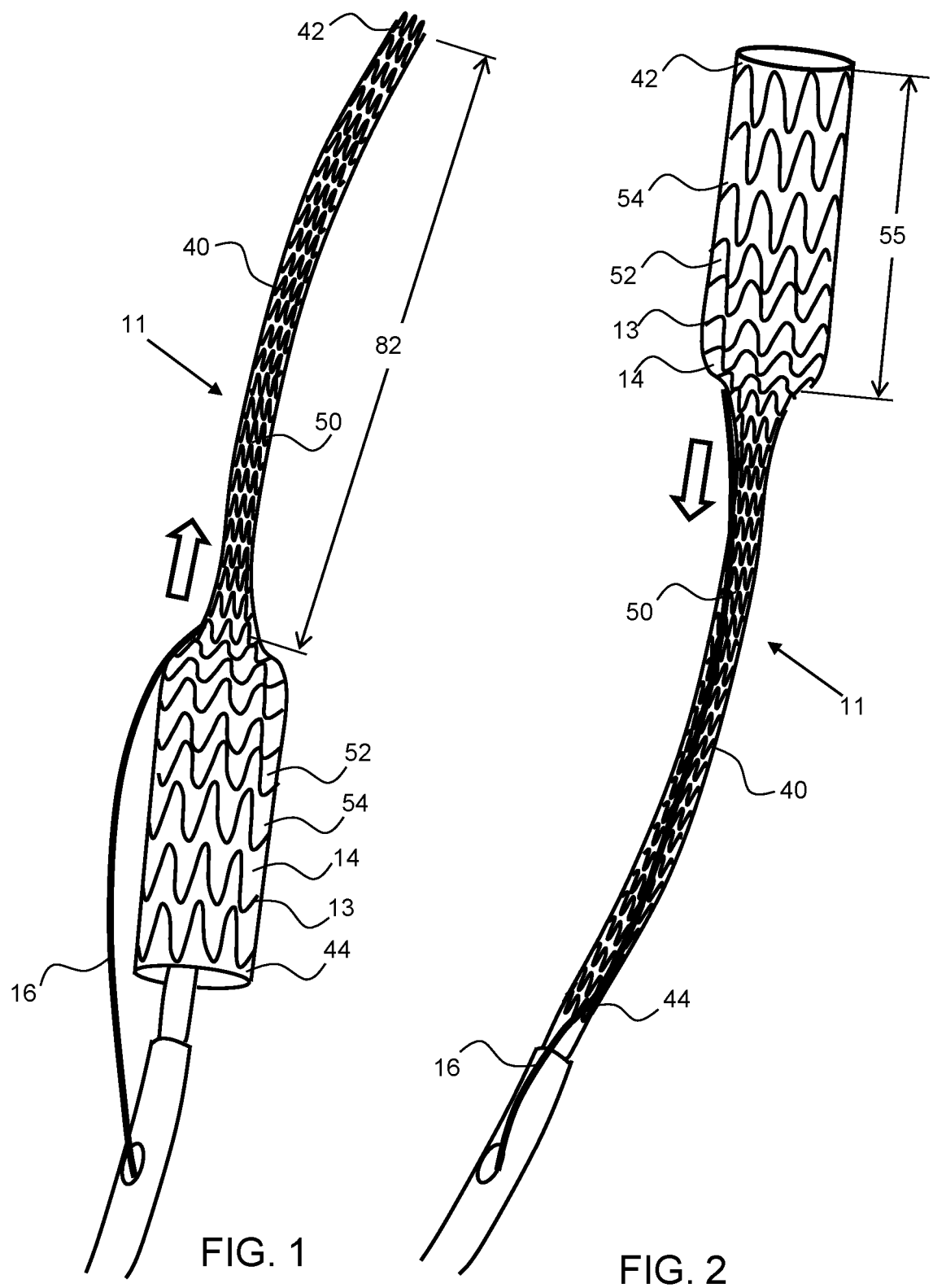

BRANCHED GRAFT ASSEMBLY METHOD IN VIVO

CROSS REFERENCE TO RELATED APPLICATIONS

This application is a continuation of U.S. patent application Ser. No. 16/686,657, filed Nov. 18, 2019, which is a divisional of U.S. patent application Ser. No. 15/441,202, filed Feb. 23, 2017, now U.S. Pat. No. 10,512,533, issued Dec. 24, 2019, which claims the benefit of priority to U.S. provisional patent application 62/298,530, filed on Feb. 23, 2016, the entirety of which are hereby incorporated by reference herein.

BACKGROUND OF THE INVENTION

Field of the Invention

The invention relates to a method of locating and deploying a branch graft from a first conduit to a second conduit, wherein the second end of the branch graft is moved in a secondary step after the first end of the branch graft is secured in the first conduit.

Background

A first dilation in an artery is known as an aneurysm. Over time, blood pressure and other factors can cause the wall to expand and it can eventually enlarge and rupture; therefore, an endovascular stent-graft is commonly used to repair aneurysms. The stent-graft system is designed to secure tightly to the lumen wall of one's artery above and below the aneurysm. Another embodiment allows for branches and fenestrations to the vessels branching off of the aorta if the aneurysm involves these vessels.

Incidence and impact of aortic aneurysms continues to grow, as indicated by the number of diagnosed cases, which is currently over 750,000 per year worldwide. In the United States alone, aortic aneurysms are the primary cause of death in approximately 11,000 cases per year and are a contributing cause of death in approximately 18,000 cases per year Endovascular repairs of aortic aneurysms are challenging and time consuming procedures, especially if the aneurysms involve branching vessels like the renal arteries or visceral arteries. Thus, stent grafts can involve a number of fenestrations or branches depending on the location of the aneurysm. In many situations, two or more access sites are required to construct a branched graft, such as one from the femoral artery, below the aneurysmal site and one from above the aneurysmal site, such from an arm access. Multiple access sites complicate the surgery and results in more trauma to the patient.

SUMMARY OF THE INVENTION

The invention is directed to a method of locating and deploying a branch graft from a first conduit to a second conduit, wherein the second end of the branch graft is moved in a secondary step, after the first end of the branch graft is secured in the first conduit, into said second conduit. The first conduit may be vessel within a living organism, such as a blood vessel within a human, or may be a conduit of another graft, such as a stent graft. The second conduit may be vessel within a living organism, such as a blood vessel within a human, or may be a conduit of another graft, such as a stent graft. In an exemplary embodiment, the first conduit is a vessel, such as a side branch from a main vessel and the second conduit is a conduit of a separate graft, thereby producing a branched graft. The second end may be configured into an aperture along the length of the main graft or into an end opening of the main graft, for example. In an exemplary embodiment, the main vessel is the aorta and the side branch vessel is a renal artery and the second end of the branch graft is configured through an aperture in the main graft. The methods described herein enable construction of a branched graft with access from one or two access locations, such as from the femoral artery and may eliminate the need for below and above the treatment site access.

In an exemplary embodiment, the first end of the branch graft is secured to the first conduit, such as a branch vessel, and the second end is subsequently moved into the second conduit and then deployed. In an exemplary embodiment, the branch graft is a stent graft, or a self-expanding stent graft that self-expands from a state having a constricted diameter to a deployed state, having an expanded diameter. The first end of the branch graft may be secured in the first conduit by pulling on a ripcord to deploy the first end of the branch graft. The second end may be then moved into the second conduit and the remaining portion of the branch graft may then be deployed. A branch graft may comprise a plurality of ripcords. In an exemplary embodiment, the branch graft comprises two ripcords, a first ripcord to deploy a first deployed portion, such as a portion from the first end, and a second ripcord to deploy a remaining portion of the length of the branch graft. In still another embodiment, a branch graft comprises three ripcords, a first ripcord to deploy a center portion of the graft, a second ripcord to deploy the portion of the branch graft that extends from the first deployed portion to the first end and a third ripcord to deploy the portion of the branch graft that extends from the first deployed portion to the second end. A branch graft may comprise any number of ripcords are required for the deployment. A branch graft may comprise a serpentine ripcord that enables a non-liner deployment of the branch graft, or a deployment that does not progress from one end to the other end. A serpentine ripcord may deploy the branch graft from the first end a first deployed length and the from the second end toward the first deployed portion. A second deployed portion may be deployed starting from a location offset from the first deployed portion. An exemplary branch graft may comprise a ripcord with a first and a second end extension, wherein the two end extensions extend from the first and second ends of the branch graft, respectively. A portion of a ripcord extension, such the first or second end extensions may extend through a locating sheath. A location sheath may enable maneuvering of the second end of the branch graft into a second conduit. The branch graft may be deployed and the locating sheath may be configured proximal to the second end of the branch graft, thereby enabling steering and guiding of the second end into a second conduit.

The second end of the branch graft may be moved into a second conduit by a tether that may be attached to a guide wire. A synch may be coupled to the tether and may be configured to couple with the branch graft proximal to the second end and then guide the second end of the branch graft into a second conduit. A synch has an opening for extending around the second end and this synch opening may be constricted to reduce the synch opening dimension and retain the branch graft therein.

A branch graft includes a graft or a stent graft or a self-expanding stent graft. A branched graft is a graft having one or more branches from a main graft conduit, such as from one or both ends or from an aperture or apertures along the length of the main graft.

The summary of the invention is provided as a general introduction to some of the embodiments of the invention, and is not intended to be limiting. Additional example embodiments including variations and alternative configurations of the invention are provided herein.

BRIEF DESCRIPTION OF THE DRAWINGS

The accompanying drawings are included to provide a further understanding of the invention and are incorporated in and constitute a part of this specification, illustrate embodiments of the invention, and together with the description serve to explain the principles of the invention.

FIGS. 1 and 2 show exemplary stent graft having a ripcord for deploying the stent from a constricted state to a deployed state.

Figure 3:
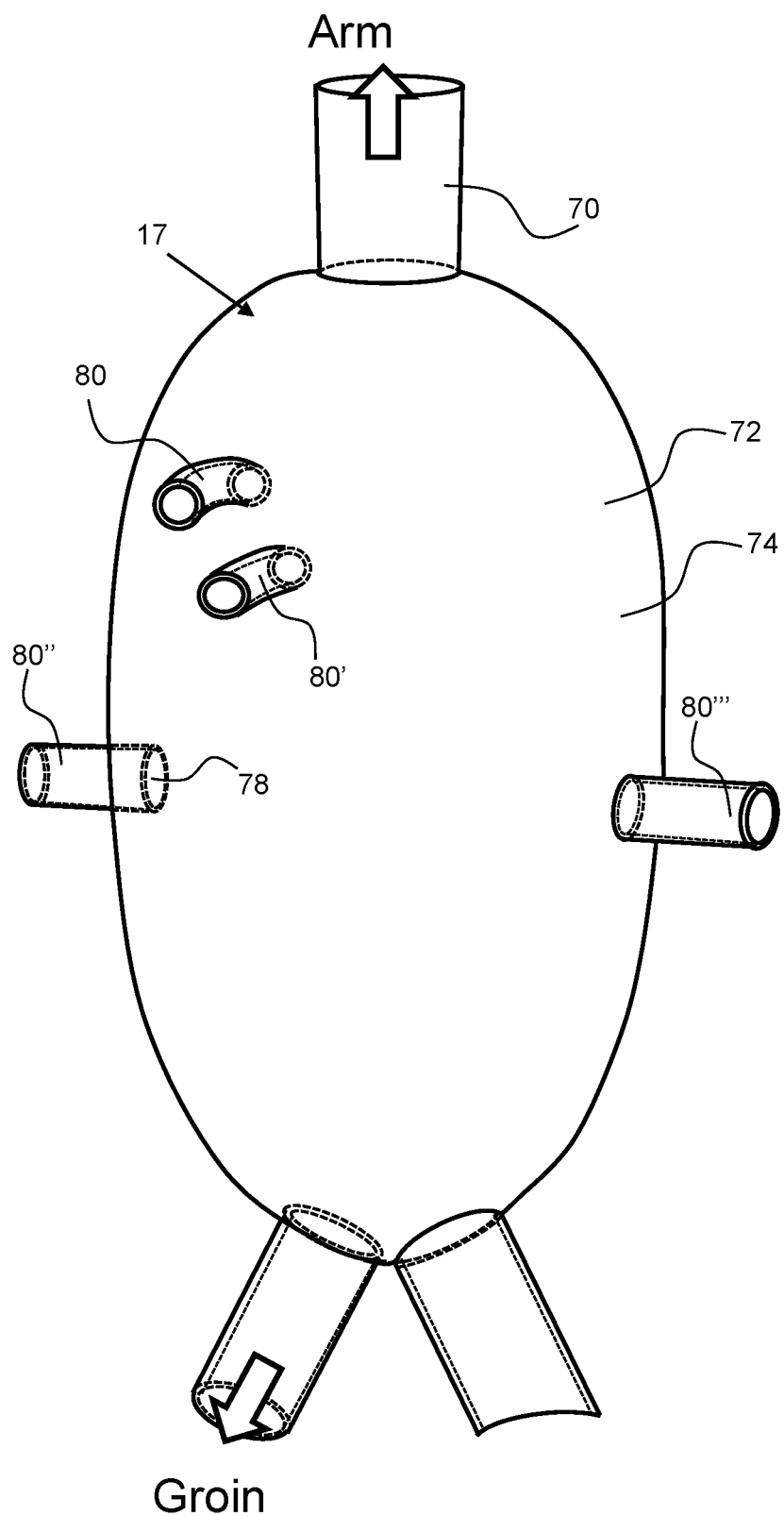
FIG. 3 shows a branched vessel having a main vessel with an aneurysm and a plurality of branch vessels.

Corresponding reference characters indicate corresponding parts throughout the several views of the figures. The figures represent an illustration of some of the embodiments of the present invention and are not to be construed as limiting the scope of the invention in any manner. Further, the figures are not necessarily to scale, some features may be exaggerated to show details of particular components. Therefore, specific structural and functional details disclosed herein are not to be interpreted as limiting, but merely as a representative basis for teaching one skilled in the art to variously employ the present invention.

DETAILED DESCRIPTION OF THE ILLUSTRATED EMBODIMENTS

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Also, use of "a" or "an" are employed to describe elements and components described herein. This is done merely for convenience and to give a general sense of the scope of the invention. This description should be read to include one or at least one and the singular also includes the plural unless it is obvious that it is meant otherwise.

Certain exemplary embodiments of the present invention are described herein and are illustrated in the accompanying figures. The embodiments described are only for purposes of illustrating the present invention and should not be interpreted as limiting the scope of the invention. Other embodiments of the invention, and certain modifications, combinations and improvements of the described embodiments, will occur to those skilled in the art and all such alternate embodiments, combinations, modifications, improvements are within the scope of the present invention.

As shown in FIGS. 1 and 2, an exemplary branch graft 40 is a stent graft 11 having a ripcord 16 for deploying the stent graft 11 from a constricted state to a deployed state. The stent graft 11 is a self-expanding stent graft, that is constricted to a constricted diameter 50. The stent 13 springs the stent graft 11 open, including both the graft 14 and the stent 13, to a deployed diameter 52 when the ripcord 16 is withdrawn to produce a first deployed portion 54 having a first deployed length 55, which may extend along the length of the stent graft 11 from the first or second ends 42, 44. In FIG. 1, the stent graft 11 is deployed from the second end 44 to towards the first end 42, or proximal to distal ends, creating an offset distance 82 from the first end 42 to the first deployed portion 54. In FIG. 2, the stent graft 11 is deployed from the first end 42 towards the second end 44 to produce a first deployed portion 54 having a first deployed length 55. Note that the stent graft 11 may deploy from the first end 42 towards the second end 44, or from the second end 44 towards the first end 42.

As shown in FIG. 3, a branched vessel 17 has a main vessel 70 with an aneurysm vessel 72 and a plurality of branch vessels 80-80'''. Each of the branch vessels 80-80'' has a vessel branch opening 78. The aneurysmal vessel 72 creates an enlarged aneurysmal conduit 74 within the main vessel 70. The main vessel 70, branch vessels 80-80'', and aneurysmal conduit 74 are all considered conduits as described herein. In an exemplary embodiment, the vessel 70 is an aortic vessel and the top of the main vessel 70 may lead upward within the body to an arm access and the bottom of the main vessel 70 may extend from the bottom to a groin access for example. The main vessel 70 may be the aorta and the branch vessels 80-80'' may include renal vessels, that lead to the kidneys.

Figure 4:
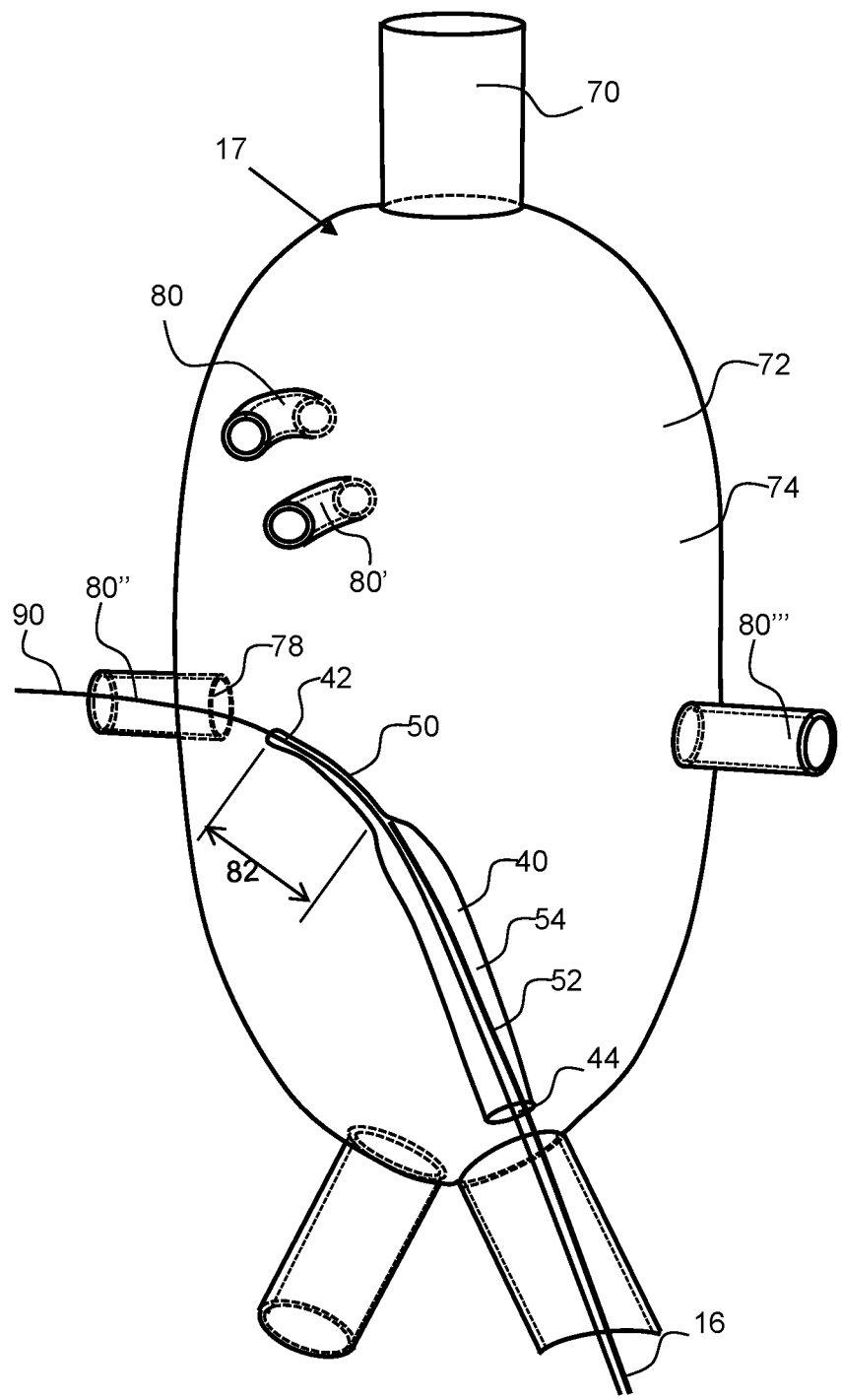
FIG. 4 shows a graft configured within the main vessel and on a guidewire.
Figure 5:
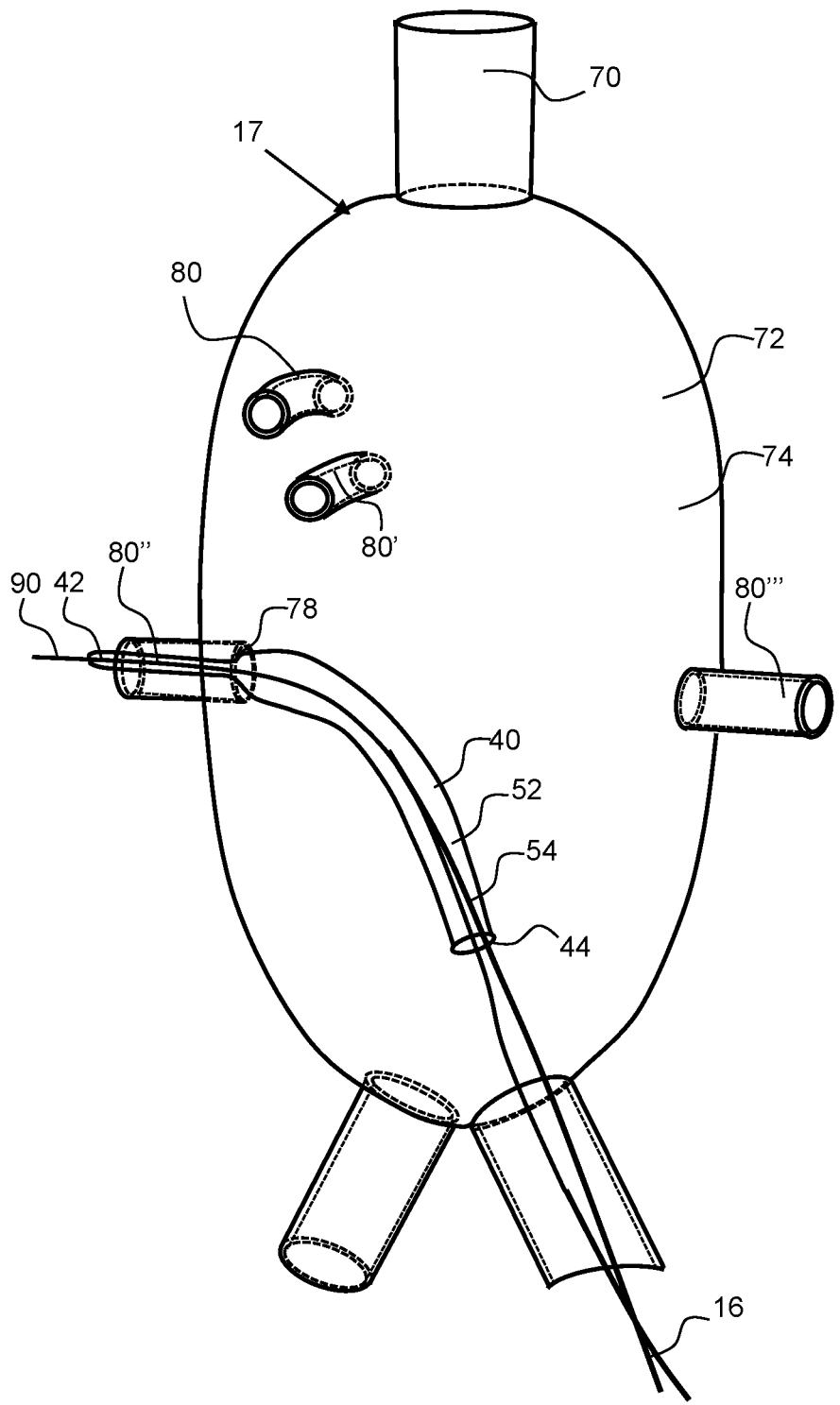
FIG. 5 shows a graft configured with a first end in a branch vessel and the second end within the main vessel.
Figure 6:
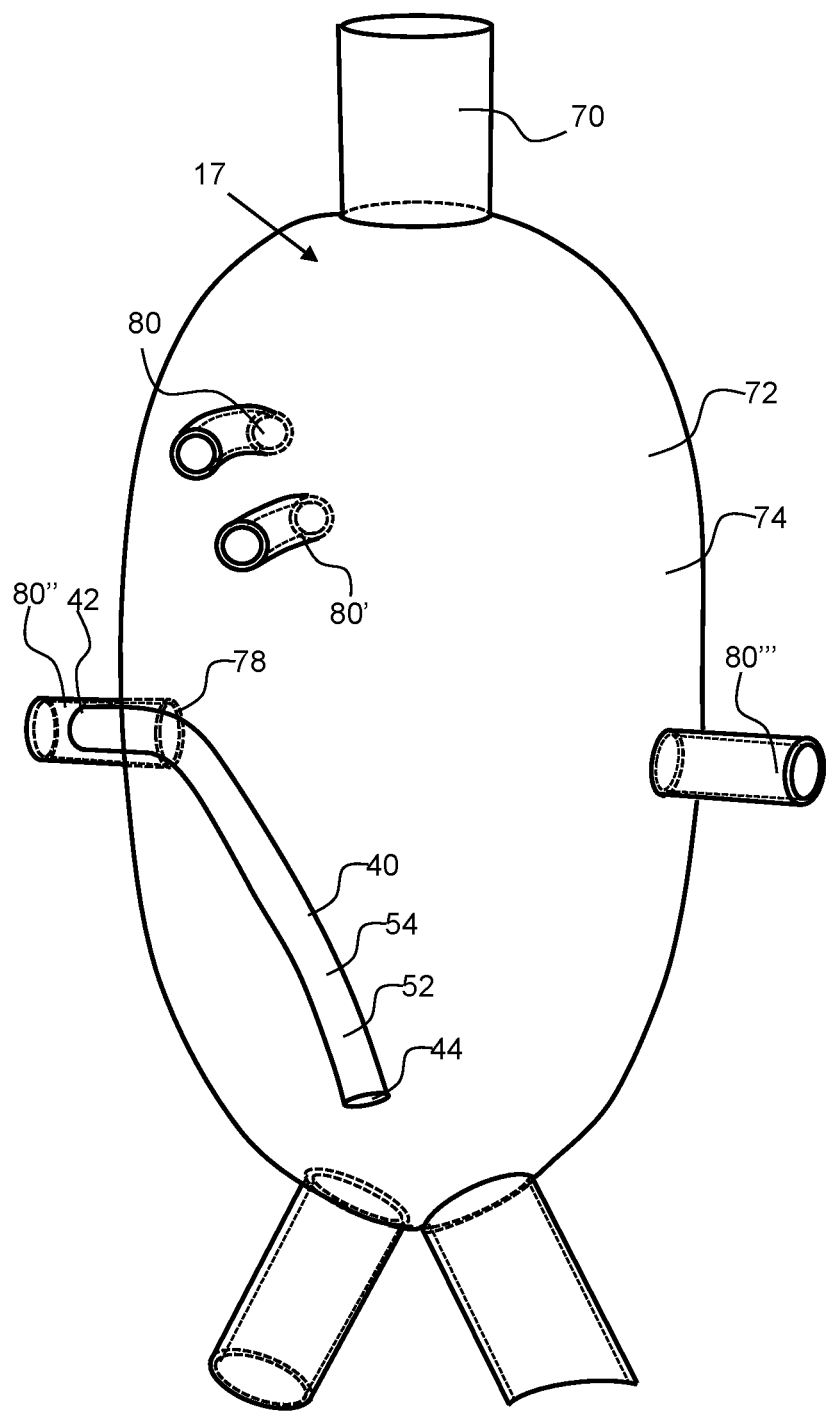
FIG. 6 shows a deployed graft configured with a first end in a branch vessel and the second end within the main vessel.

Referring now to FIGS. 4 to 6, a branch graft 40 is configured within the main vessel 70 and on a guidewire 90. As shown in FIG. 4, the branch graft 40 is partially deployed from the second end 44, creating a first deployed portion 54 and leaving the first end 42 at a constricted diameter 50. A ripcord 16 may be used to deploy a self-expanding stent graft 11 from an offset distance 82 from the first end 42. This offset distance 82 may be the desired insertion distance into the target branch vessel 80''. As shown in FIG. 5, the branch graft 40 is configured with a first end 42 in a branch vessel 80'' and the second end 44 within the enlarged aneurysmal conduit 74 of the aneurysmal vessel 72. The enlarged deployed diameter 52 of the first deployed portion 54 prevents this portion 54 of the graft 40 from being inserted into the branch vessel 80'', or target vessel, as it is oversized or larger in diameter than the vessel branch opening 78 of the target branch vessel 80''. As shown in FIG. 6, the first end 42 of the branch graft 40 is deployed to secure the branch graft 40 to the branch vessel 80''. The ripcord 16 may be a serpentine ripcord that extends from a position along the length of the stent graft 11 toward the second end 44 and then back toward the first end 42.

Figure 7:
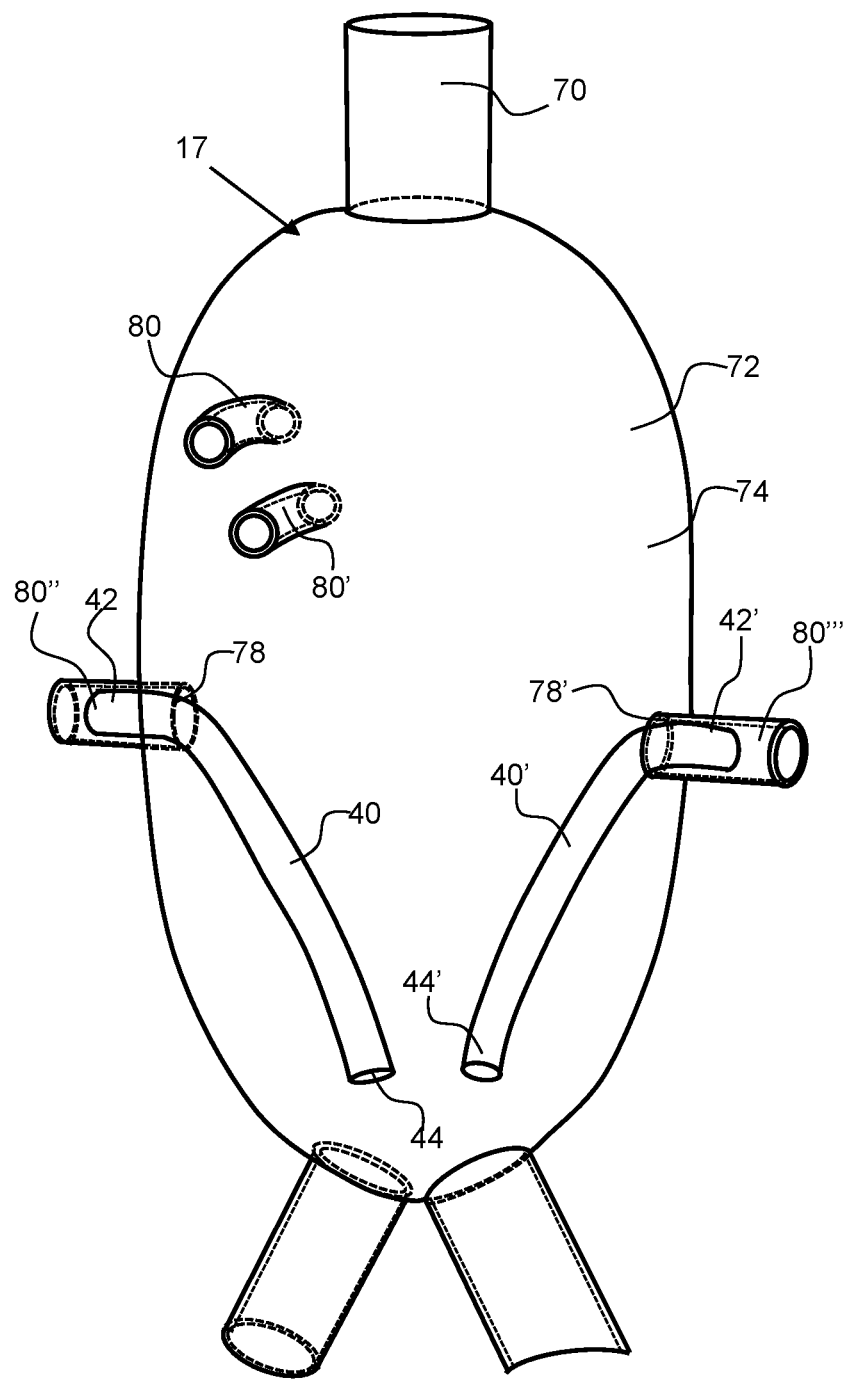
FIG. 7 shows two deployed grafts configured with their first ends in branch vessels and their second ends within the main vessel.
Figure 8:
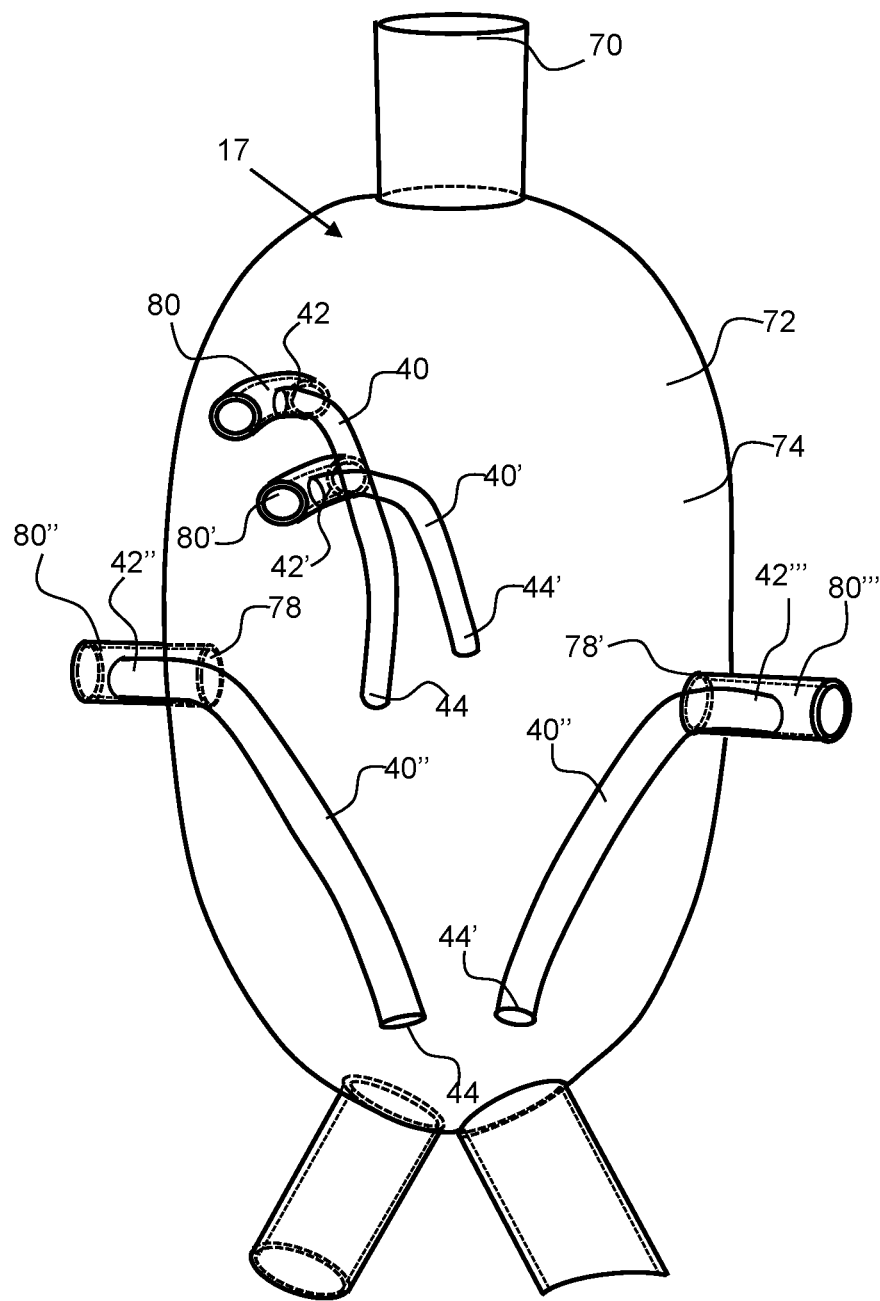
FIG. 8 shows four deployed grafts configured with their first ends in branch vessels and their second ends within the main vessel.
Figure 9:
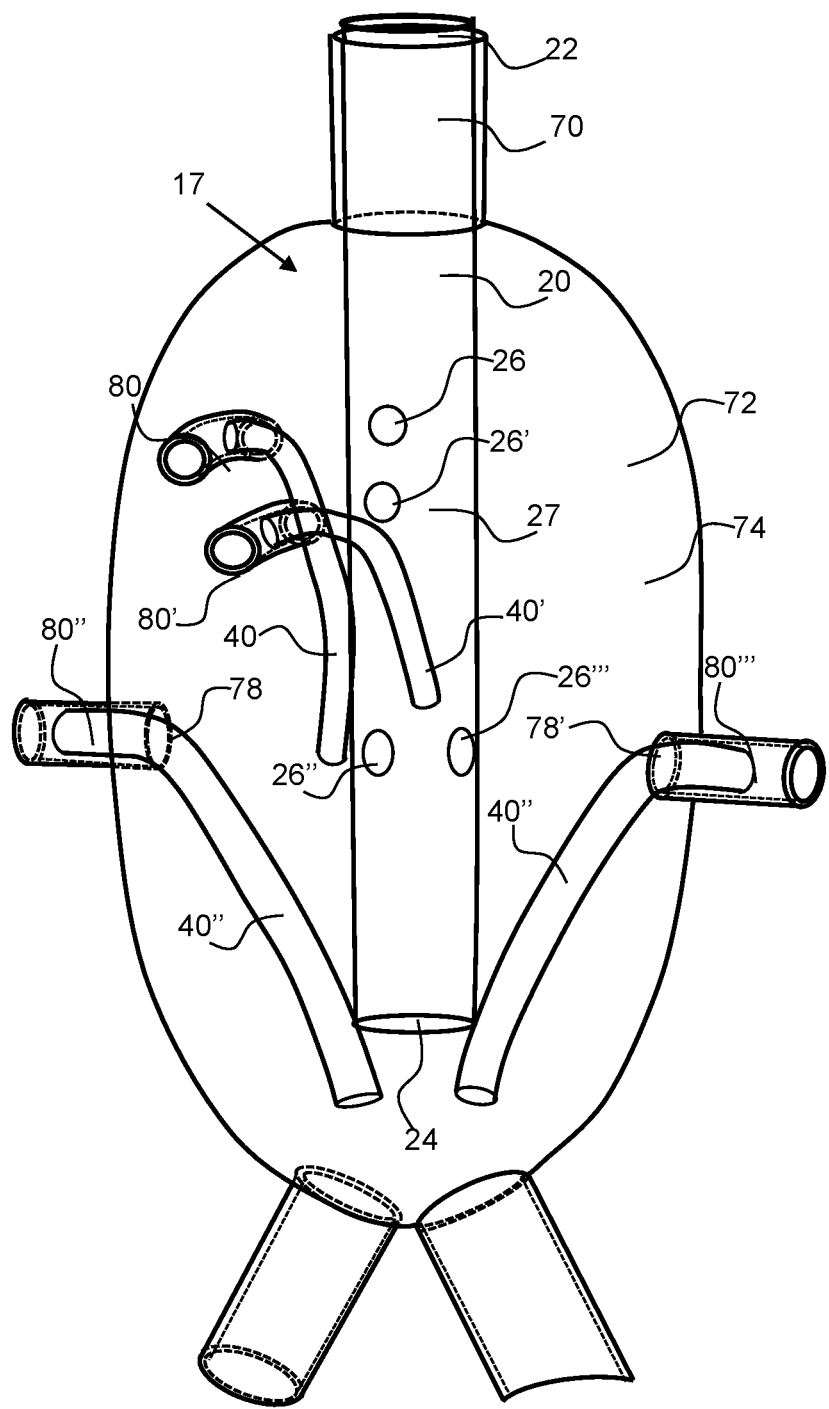
FIG. 9 shows four deployed grafts configured with their first ends in branch vessels and their second ends within the main vessel and a main graft configured along the main vessel and extending past the vessel branch openings.

As shown in FIG. 7, two branch grafts 40, 40' are coupled to branch vessels 80'', 80''' respectively, and their second ends 44, 44' are within the enlarged aneurysmal conduit 74 of the aneurysmal vessel 72. As shown in FIG. 8, four branch vessels 40-40''' are coupled to branch vessels 80-80'' respectively, and their second ends 44-44'' are within the enlarged aneurysmal conduit 74 of the aneurysmal vessel 72.

Figure 10:
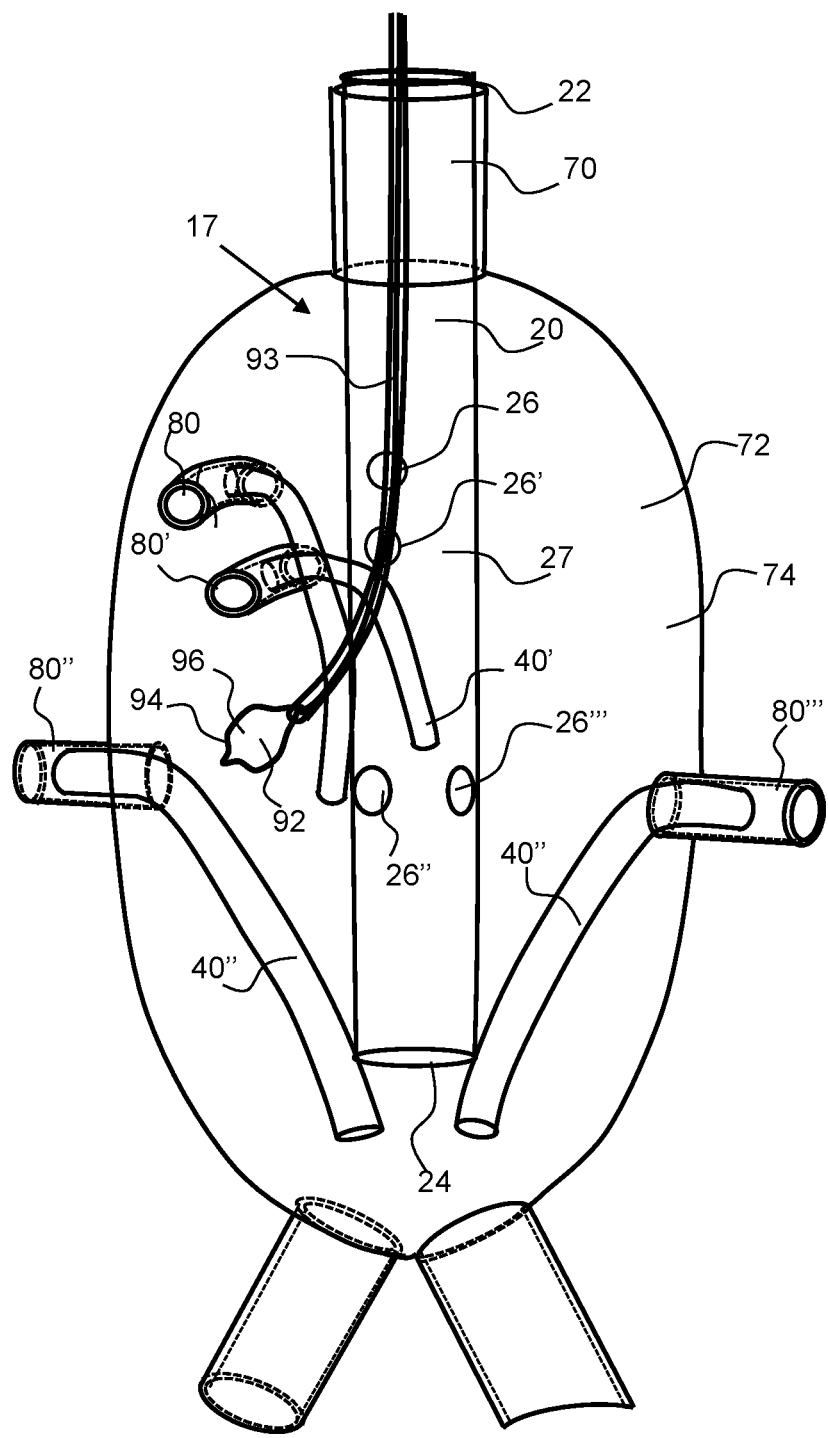
FIG. 10 shows a tether extending down the main vessel, within the main graft and extending out of one of the main graft apertures.
Figure 11:
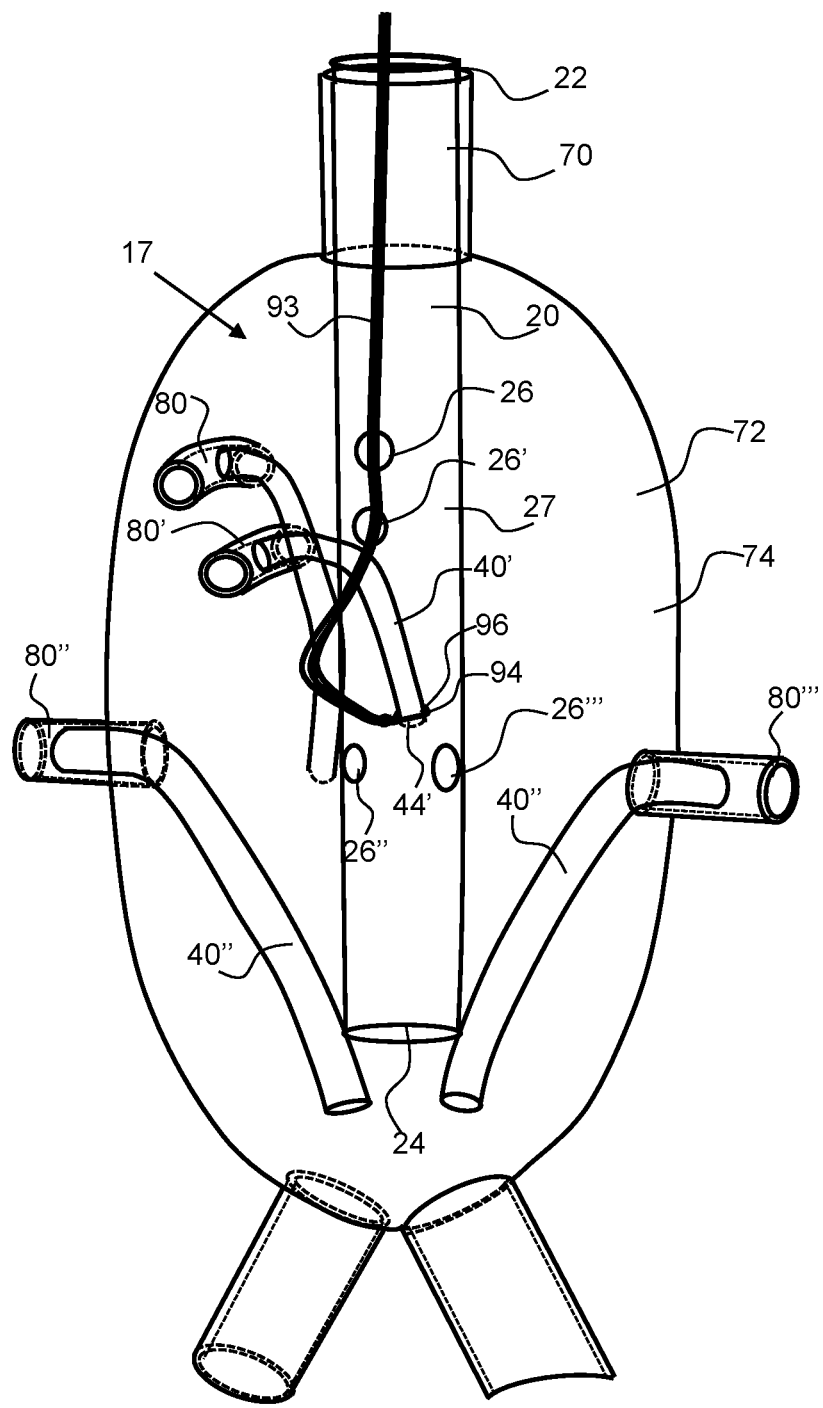
FIG. 11 shows a tether having a synch extended around the second end of one of the branch grafts.
Figure 12:
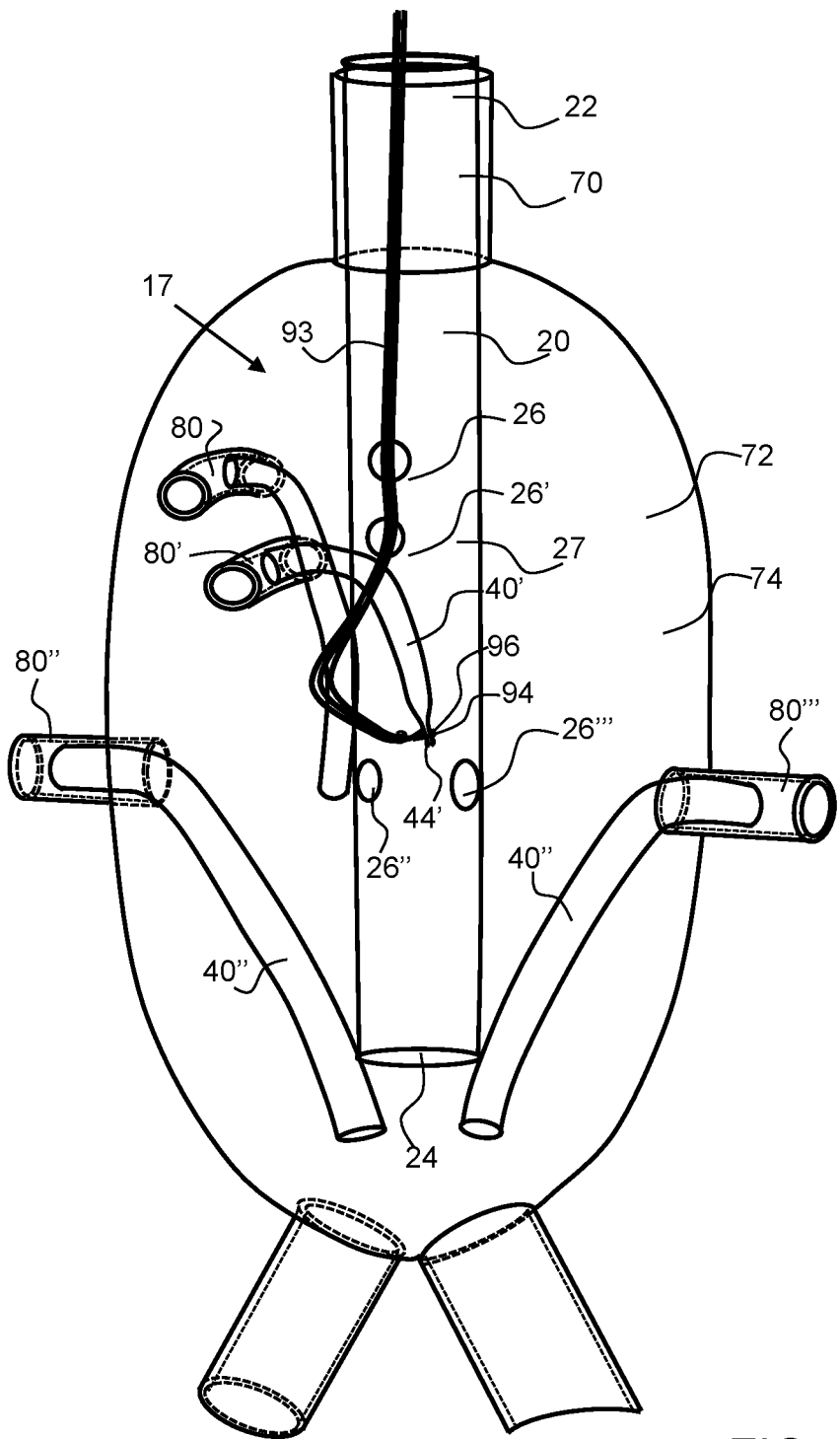
FIG. 12 shows a tether with the synch collapsed to reduce the second end diameter of the branch graft.
Figure 13:
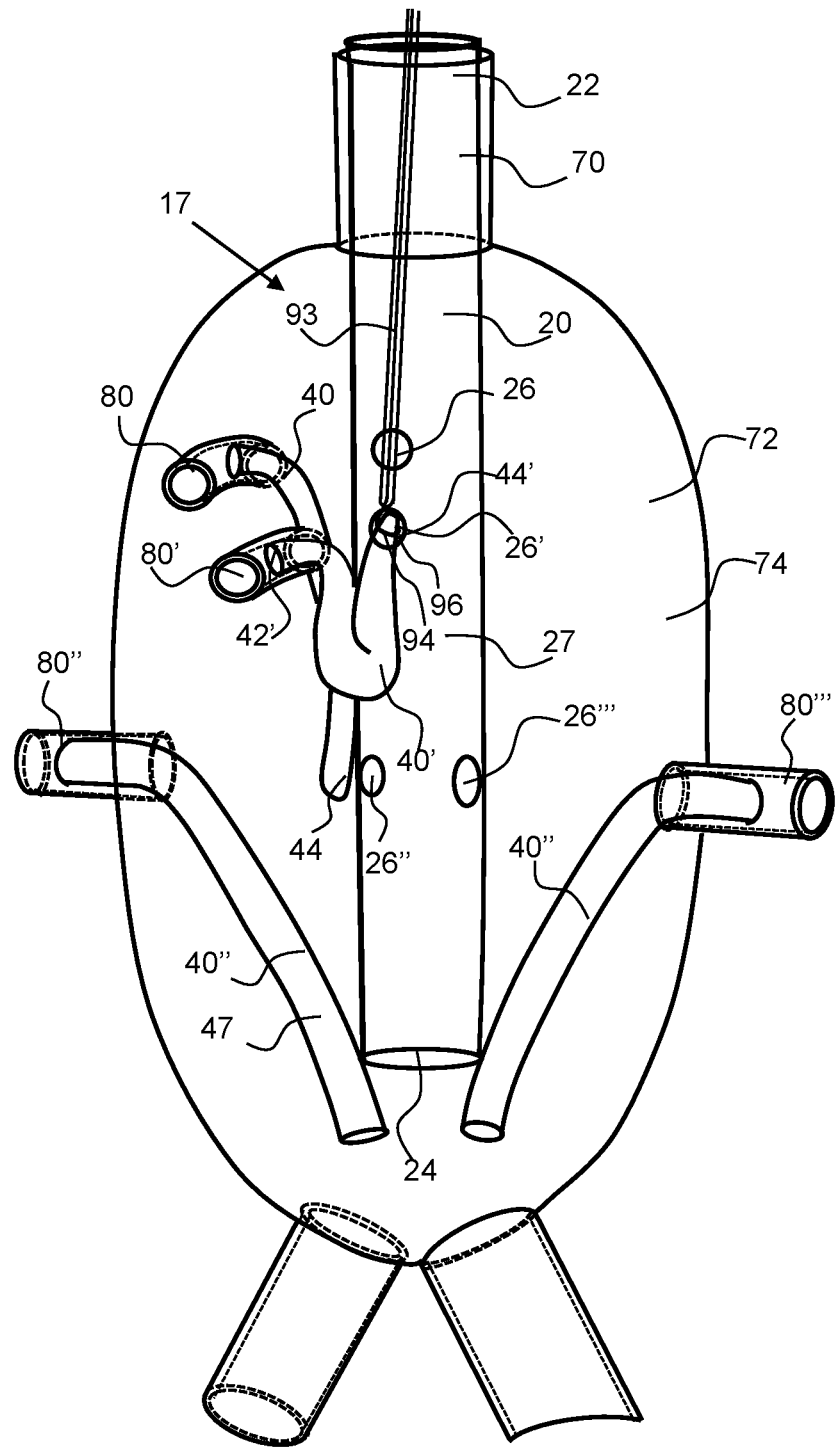
FIG. 13 shows a tether pulling the second end of the branch graft through the main graft aperture and into the conduit of the main graft.
Figure 14:
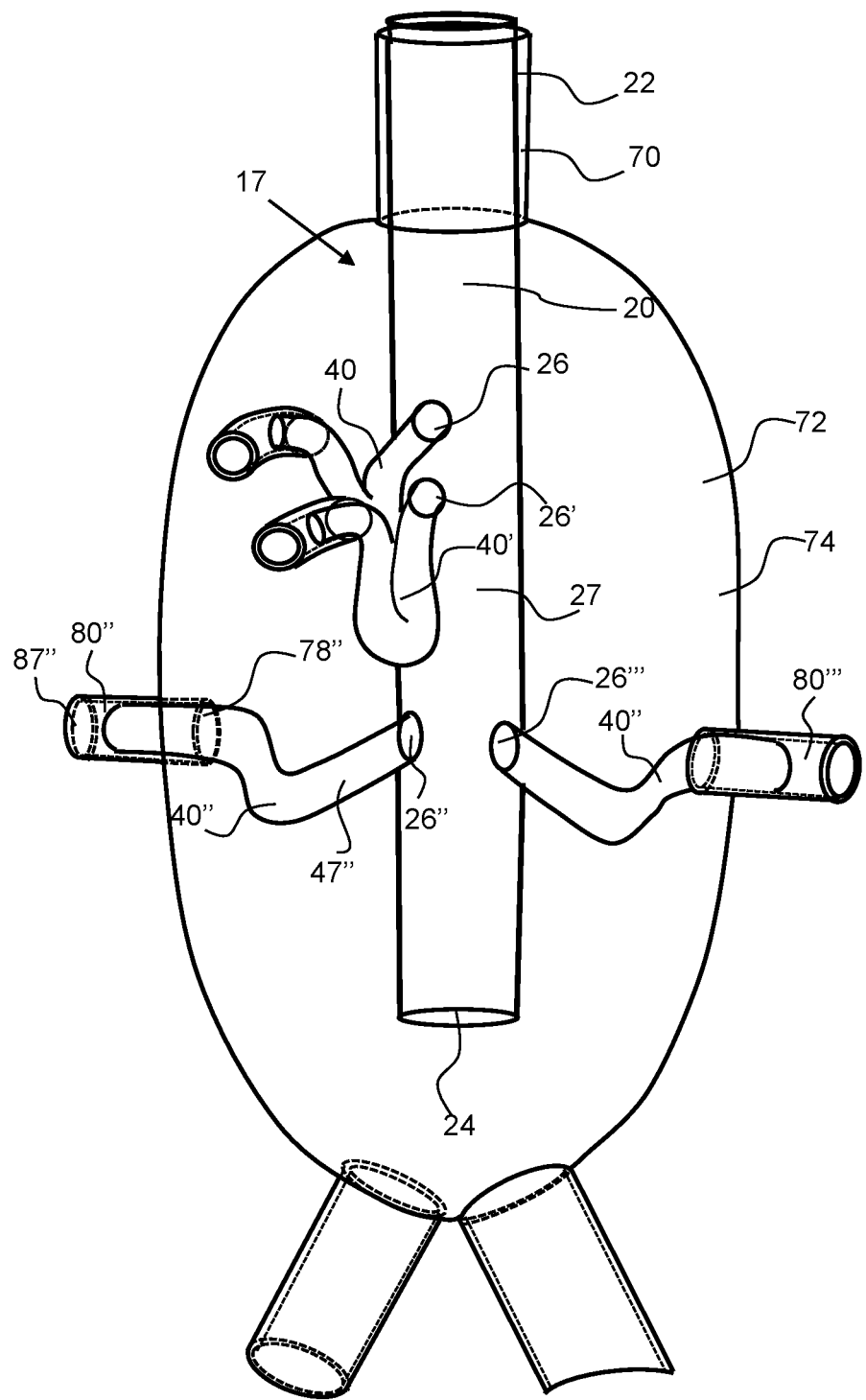
FIG. 14 shows a plurality of branch grafts with their first ends coupled to the branch vessels and their second ends coupled to the main graft at the apertures.

Referring now to FIGS. 9 to 14, a main graft 20 is deployed within the enlarged aneurysmal conduit 74 of the aneurysmal vessel 72. The main graft 20 extends past the branch vessels 80-80'' and has a plurality of apertures 26-26''. The main graft includes a first end 22 and a second end 24. As shown in FIG. 10 a tether 92 is extended down through the main graft 20 and out one of the apertures 26' and into the conduit 74 of the main vessel 70. The tether 92 is couple to a tether line 93 and has a cinch 94 on the extended end. The cinch 94 has a cinch opening 96 for retaining a branch graft 40. As shown in FIG. 11, the second end 44' of branch graft 40' is retained within the cinch opening 96. As shown in FIG. 12, the cinch opening 96 is reduced to a constricted state and thereby reduces the diameter of the second end 44' of branch graft 40'. As shown in FIG. 13, the tether 92 is withdrawn to move the second end 44' of branch graft 40' into the aperture 26' in the main graft 20. The cinch can then be released to couple the second end 44' of the branch graft 40' to the main graft 20, wherein the second end 44' of the branch graft 40' is within the conduit 27 of the main graft 20. The branch graft 40' will then create a fluid conduit from the main graft 20 to the branch vessel 80'. It is to be understood that the second end 44' of the branch graft 40' may be drawn into the second end 24 of the main graft 20 to produce a connecting conduit from the second end 24 of the main conduit 27 to the branch vessel 40'. The second end 24 of the main conduit 27 may comprise a branch with two openings and separate branch grafts 40 may be coupled to each of the two openings and extend to separate branch vessels 80, for example. As shown in FIG. 14, all four of the branch grafts 40-40''' are coupled with the main graft 20 through the main graft apertures 26-26'', respectively. The branch grafts 40-40'' couple the conduit 27 of the main graft 20 with the conduits 87-87'' of the branch vessels 80-80''. Branch graft 40'' has a conduit 47'' that couples the main graft conduit 27 from the main graft aperture 26'' to the branch vessel conduit 87'' through the vessel branch opening 78'' of the branch vessel.

Figure 15:
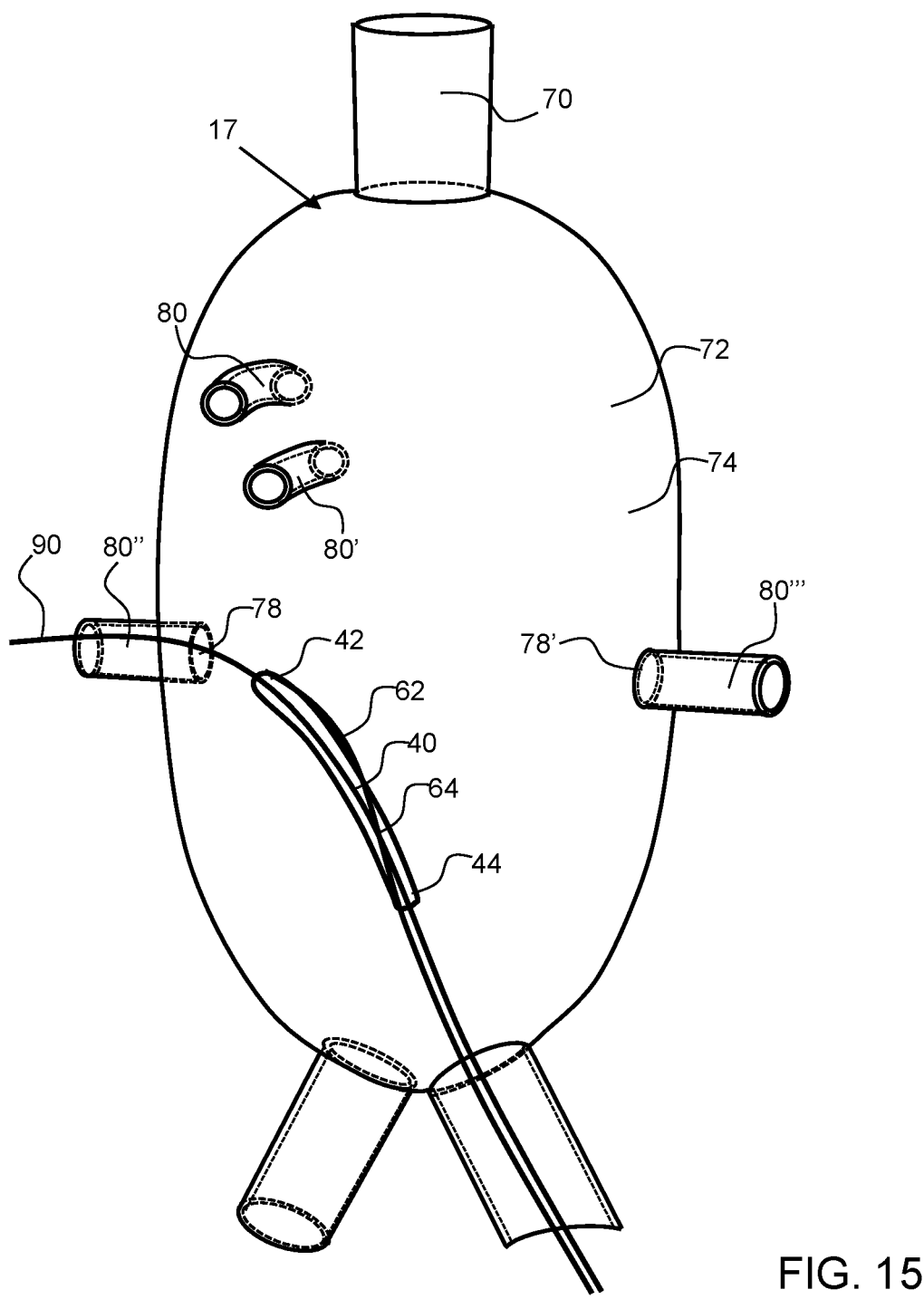
FIG. 15 shows a graft having two ripcords configured within the main vessel and on a guidewire.
Figure 16:
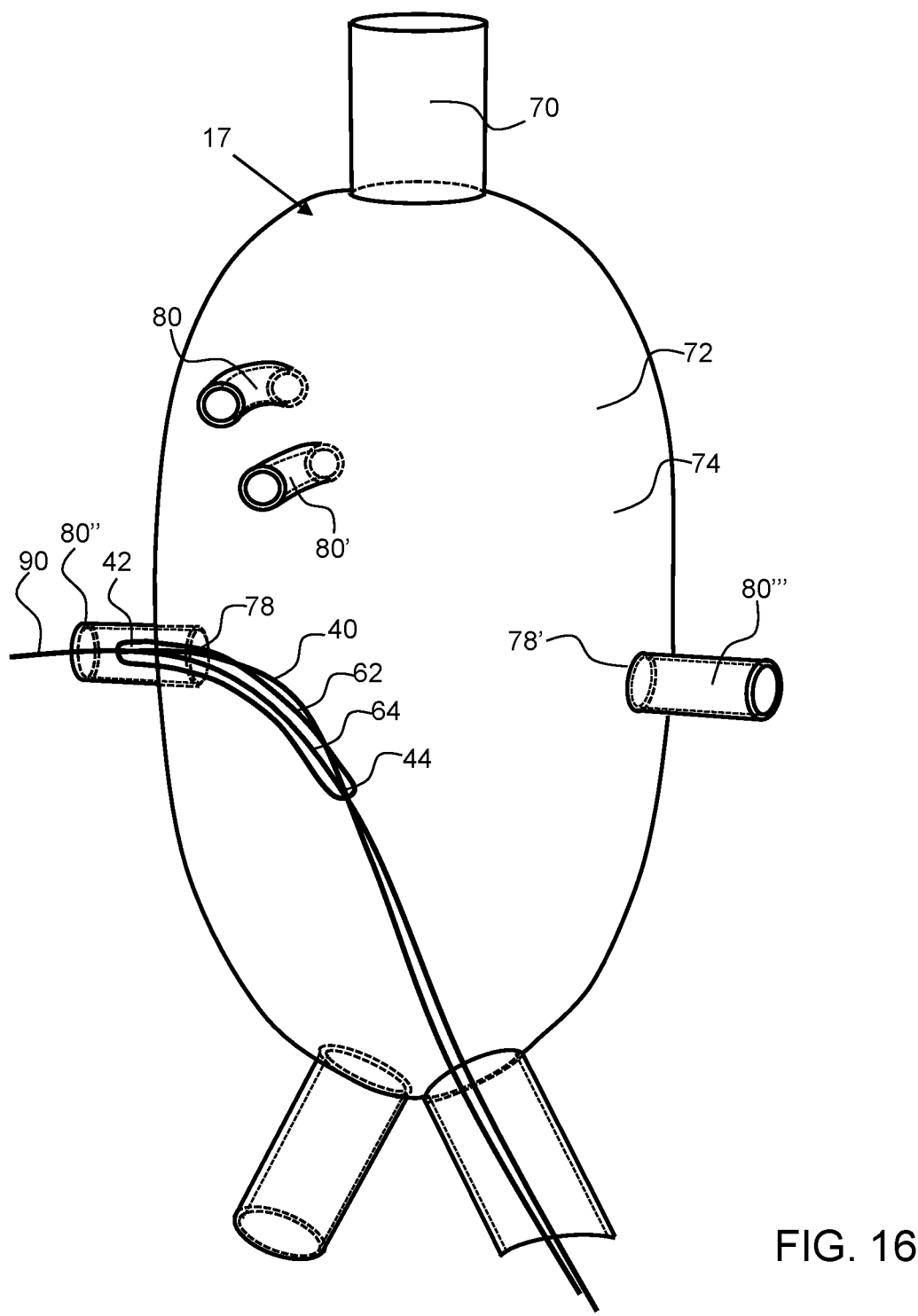
FIG. 16 shows a graft having two ripcords with the first end configured within a branch vessel.
Figure 17:
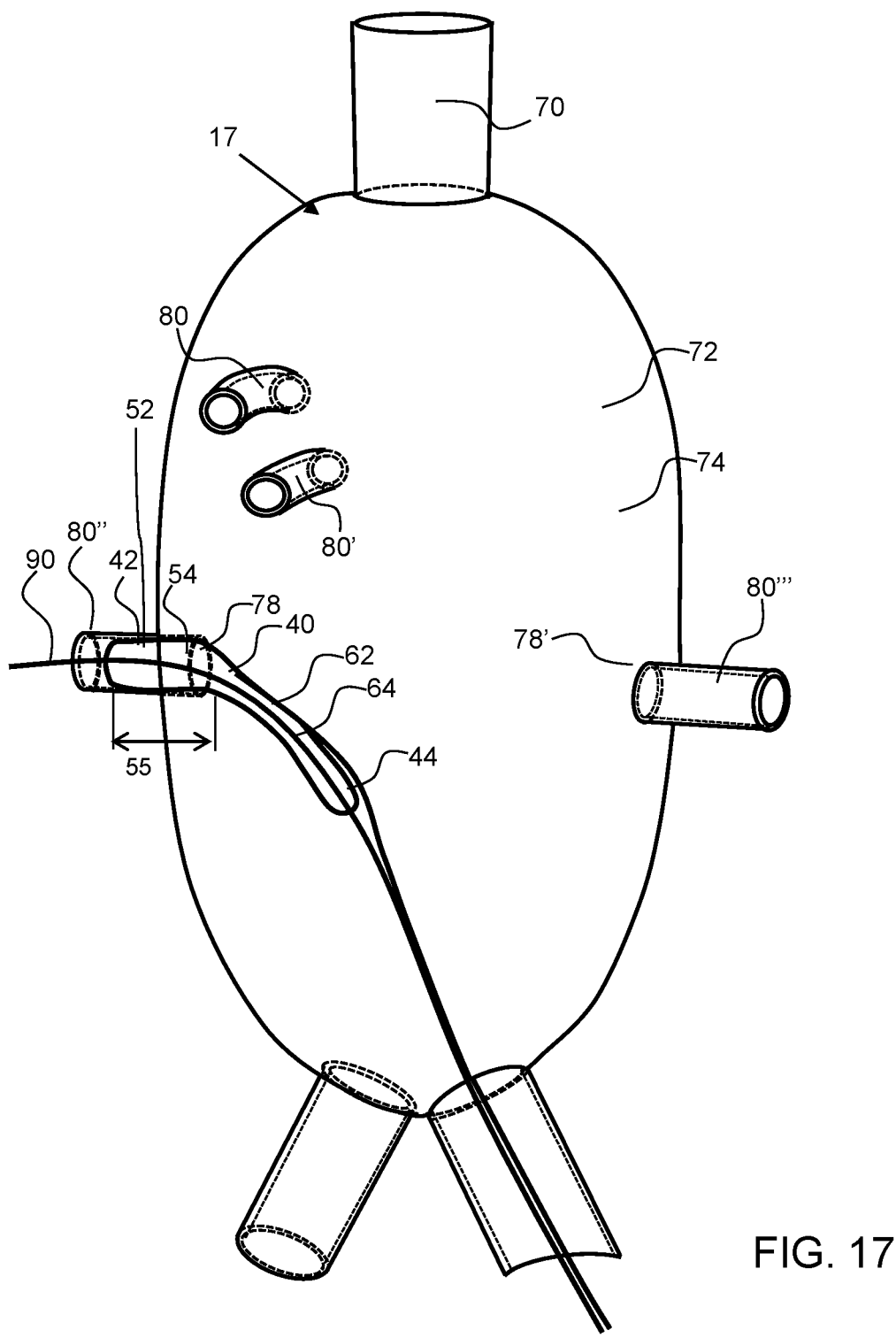
FIG. 17 shows a graft having two ripcords configured within a branch vessel and partially deployed, with a first ripcord being withdrawn to produce a first deployed portion in the branch vessel.
Figure 18:
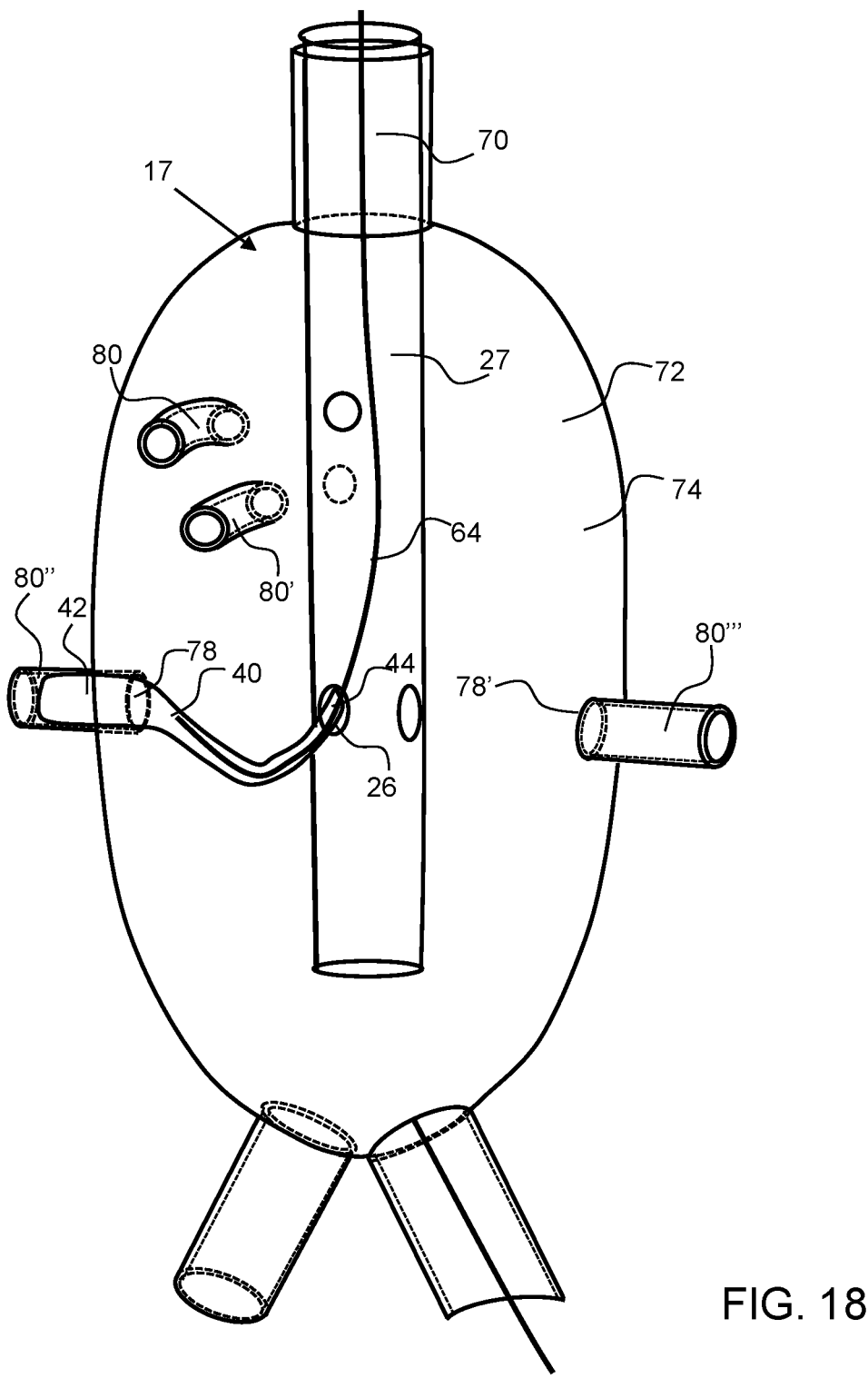
FIG. 18 shows a graft having two ripcords configured within a branch vessel and partially deployed, with a first deployed portion in the branch vessel and the second end being drawn into the main graft through an aperture by a ripcord.
Figure 19:
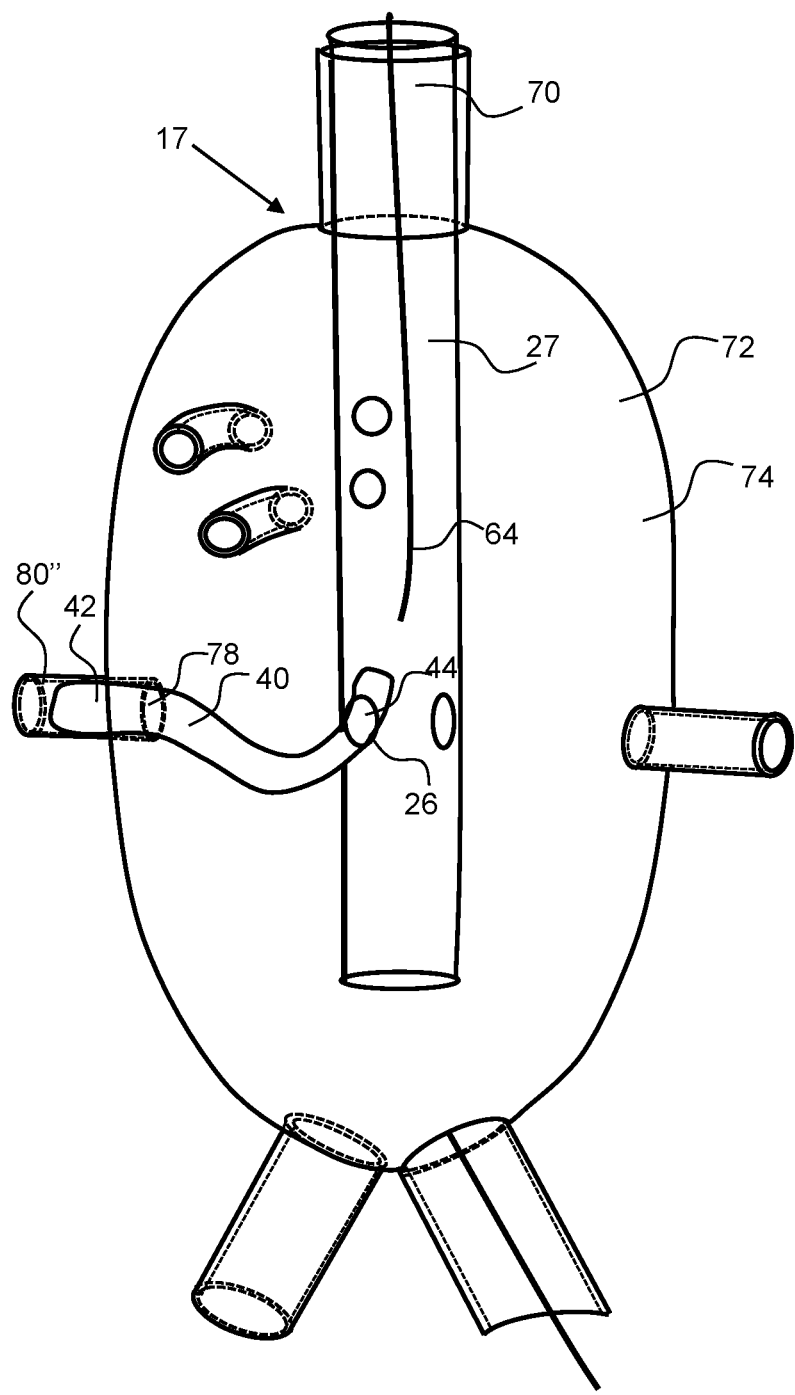
FIG. 19 shows the graft of FIG. 18, with the second ripcord pulled from the graft to deploy the remaining portion of the graft and couple the graft to the main graft.

Referring now to FIGS. 15 to 19, a branch graft comprising two ripcords is configured and deployed between an aperture in a main graft and a branch vessel. As shown in FIG. 15, an exemplary branch graft 40 has two ripcords 62, 64. The branch graft 40 is configured within the main vessel 70 by a guidewire 90. As shown in FIG. 16, the first end 42 of the branch graft 40 is configured within the target branch graft 80'' and in FIG. 17 the first ripcord 62 is withdrawn to deploy the first end 42 of the branch graft 40 to a deployed diameter 52 to retain the first end 42 in the branch vessel 80. The first deployed portion 54 extends from the first end 42 a first deployed length 55. As shown in FIG. 18, the second end 44 of the branch graft 40 has been moved into the aperture 26 of the main graft 20. The second end 44 of the branch graft 40 may be moved by the second ripcord 64 and then deployed by pulling and withdrawing the second ripcord 64. As shown in FIG. 19, the second ripcord 64 is pulled to deploy the remaining length of the branch graft 40, the length from the second end 44 to the first deployed portion 54. The second ripcord 64 may be configured to deploy the remaining length of the branch graft 40 from the second end 44 toward the first end 42, or from the first deployed portion 54, toward the second end 44. The second end 44 may be inserted into the conduit 27 of the main graft 27 by any means described herein, including a tether of by way of a locating sheath.

Figure 20:
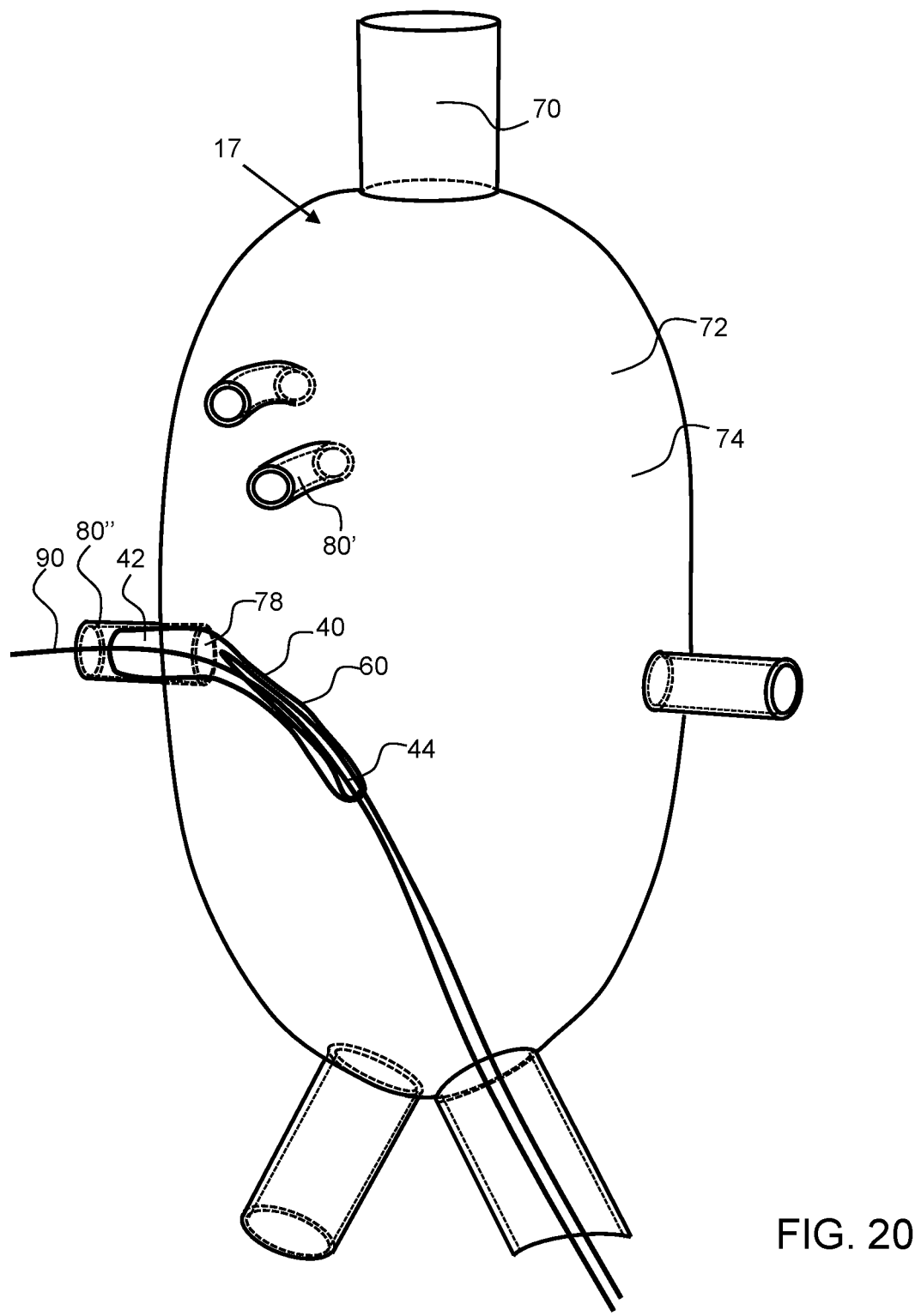
FIG. 20 shows a graft having a serpentine ripcord configured with a first end in a branch vessel and the serpentine ripcord partially withdrawn to produce a first deployed portion in the branch vessel.
Figure 21:
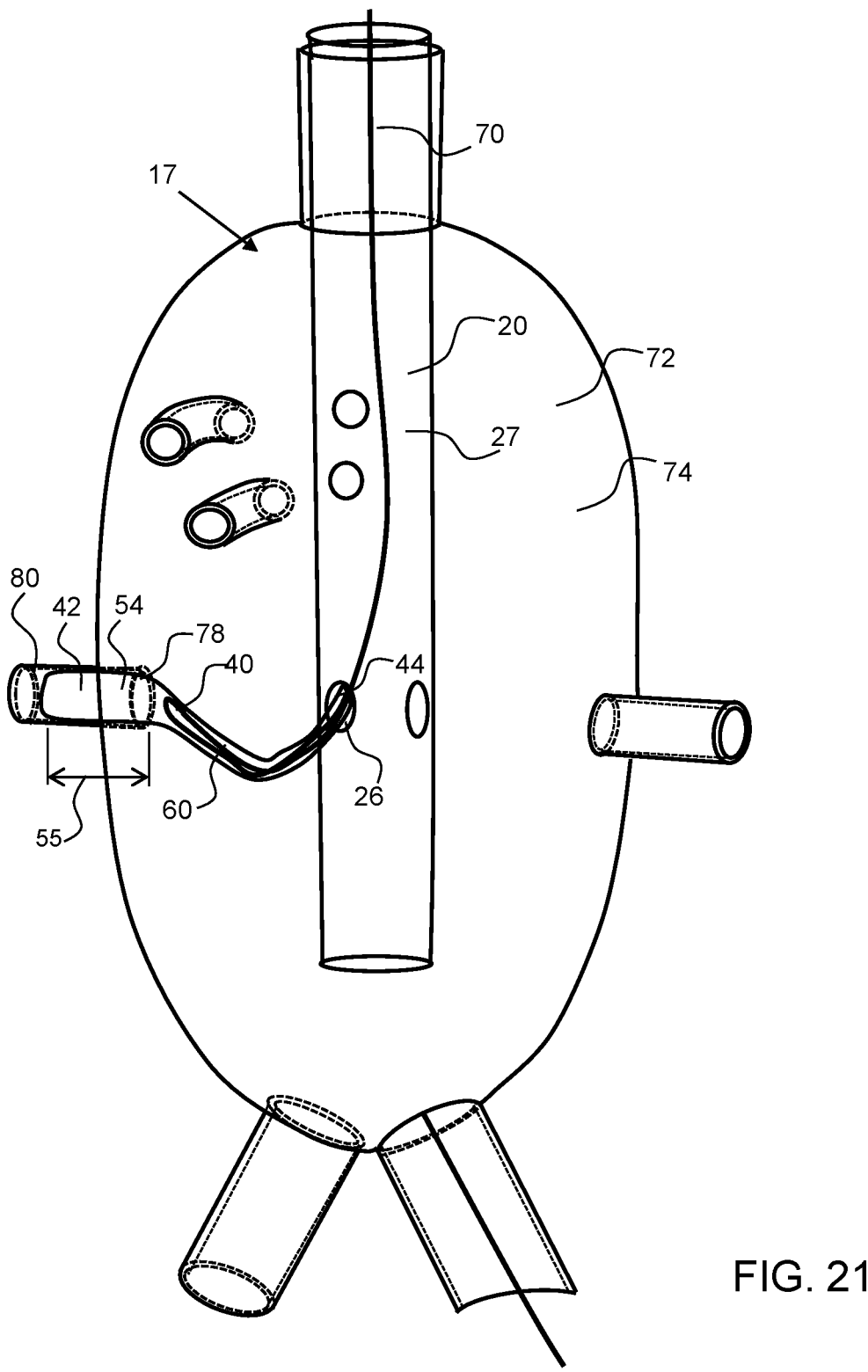
FIG. 21 shows the graft of FIG. 20, with the second end configured in the conduit of the main graft.
Figure 22:
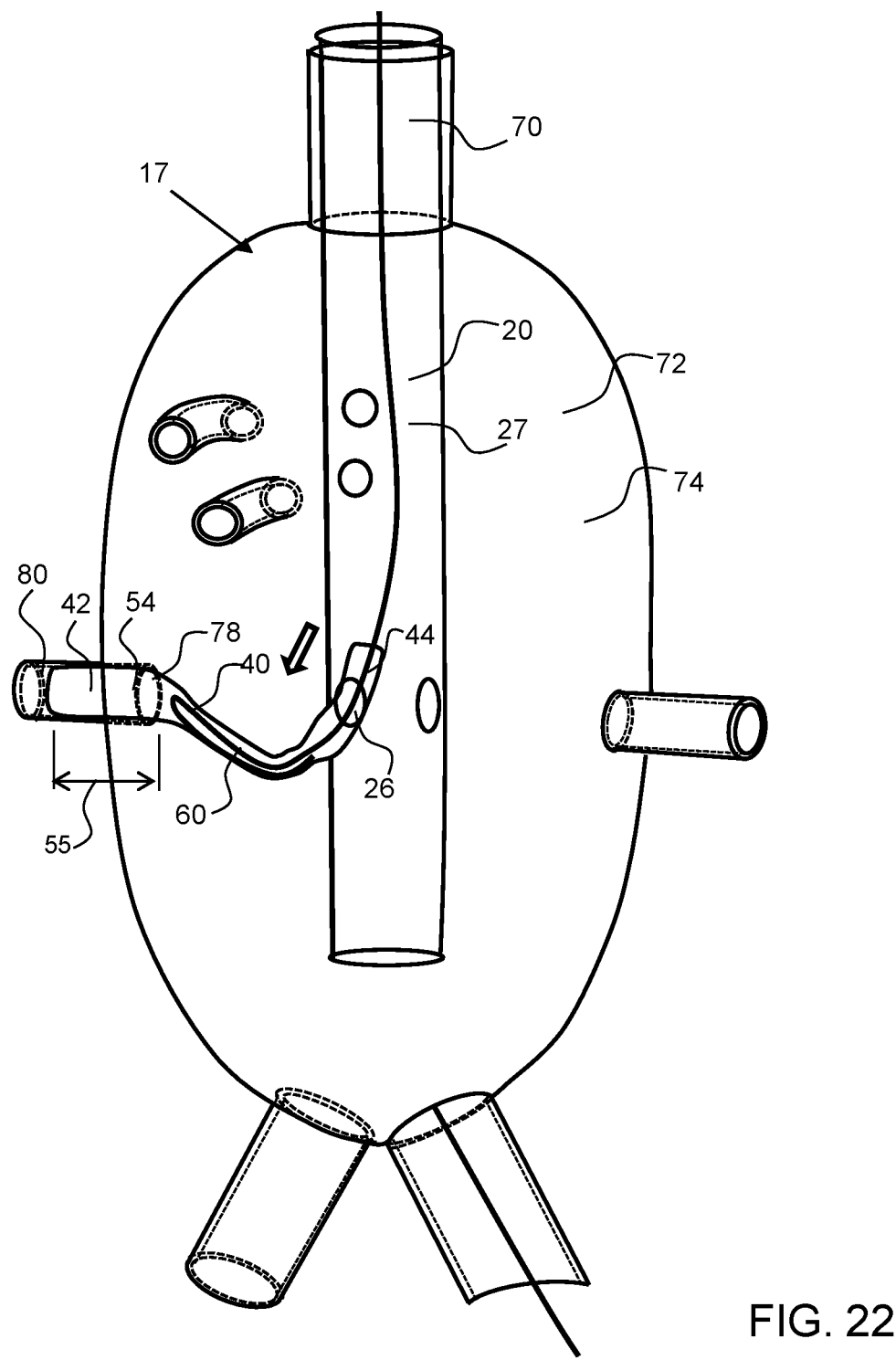
FIG. 22 shows the graft of FIG. 21, with the second end being deployed by the withdraw of the ripcord, wherein the branch graft deploys from the second end toward the first end.

Referring now to FIGS. 20 to 22, a branch graft 40 has a serpentine ripcord 60 that enables the branch graft 40 to deploy in two or more sections. As shown in FIG. 20, the first end 42 of the branch graft 40 is configured within a branch vessel 80". The first end 42 of the branch graft 40 is deployed by pulling and withdrawing the serpentine ripcord 60 a portion of the length from the branch graft 40. As shown in FIG. 21, the second end 44 of the branch graft 40 shown in FIG. 20 is now moved into the conduit 27 of the main graft 20 through the main graft aperture 26. As shown in FIG. 22, the serpentine ripcord 60 is being withdrawn and is deploying the branch graft 40 from the second end 44 toward the first deployed portion 54 to fully deploy the branch graft 40. Note that the serpentine ripcord 60 extends from a position proximal the first end 42, down to the second end 44 and then back along the length of the branch graft 40 toward the first end 42 to allow this two phased or two section deployment that is non-continuous along the length of the branch graft 40, not continuous from one end to the other.

Figure 23:
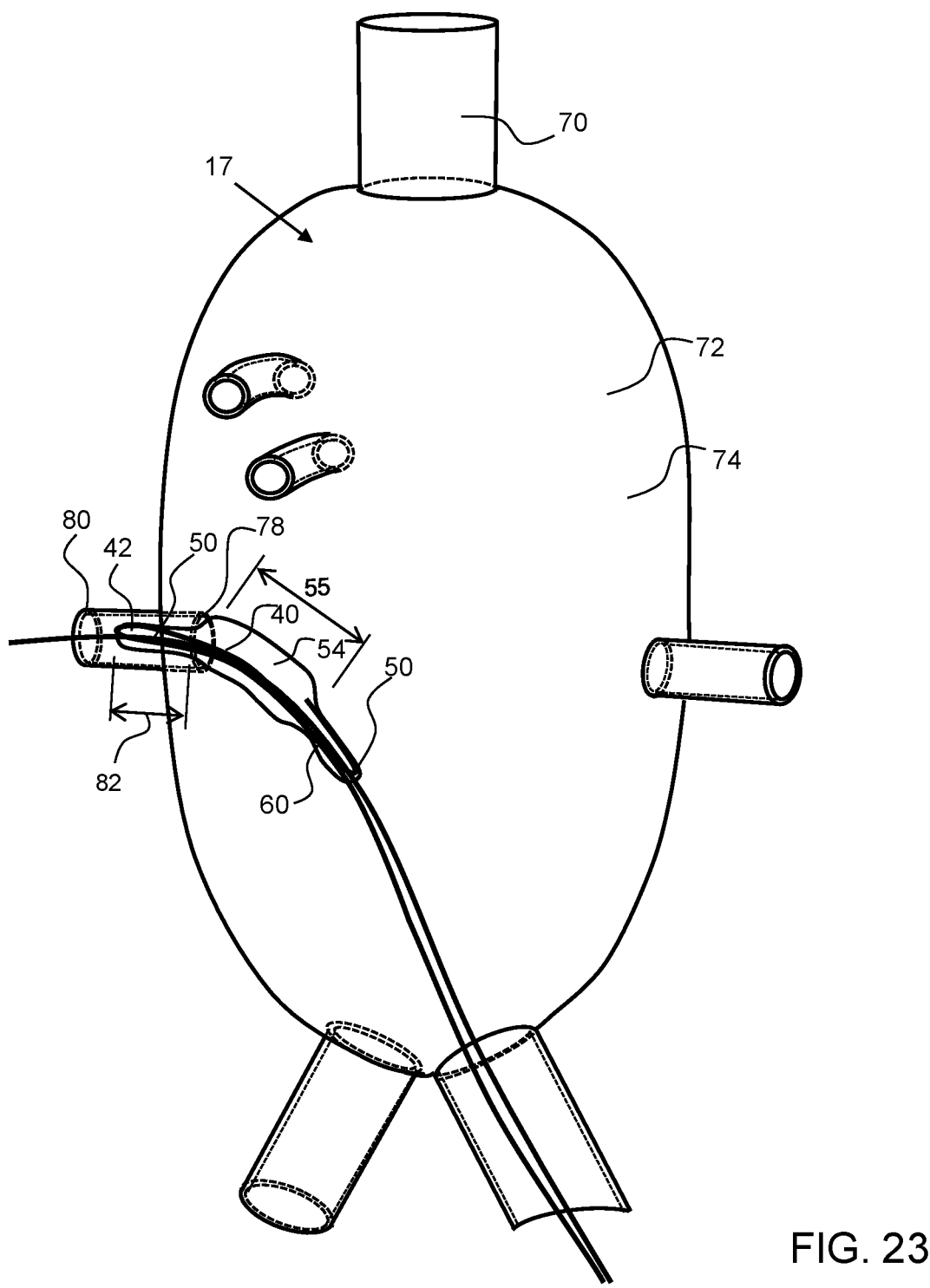
FIG. 23 shows a graft having a serpentine ripcord configured with a first end in a branch vessel and the serpentine ripcord partially withdrawn to produce a first deployed portion along a middle portion of the branch graft.
Figure 24:
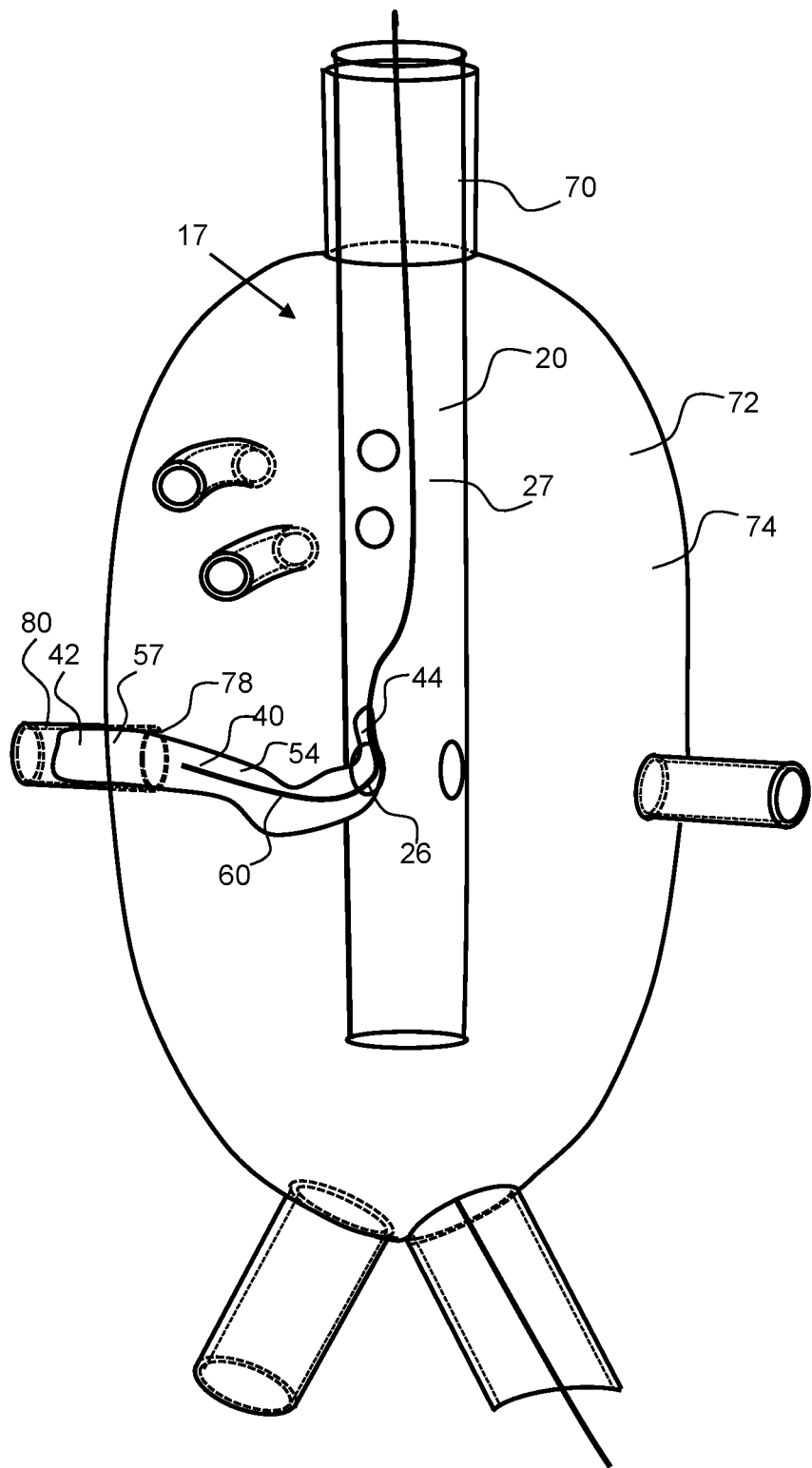
FIG. 24 shows the graft of FIG. 23, with the second end configured in the conduit of the main graft and the serpentine ripcord withdrawn to deploy the first end within the branch vessel.
Figure 25:
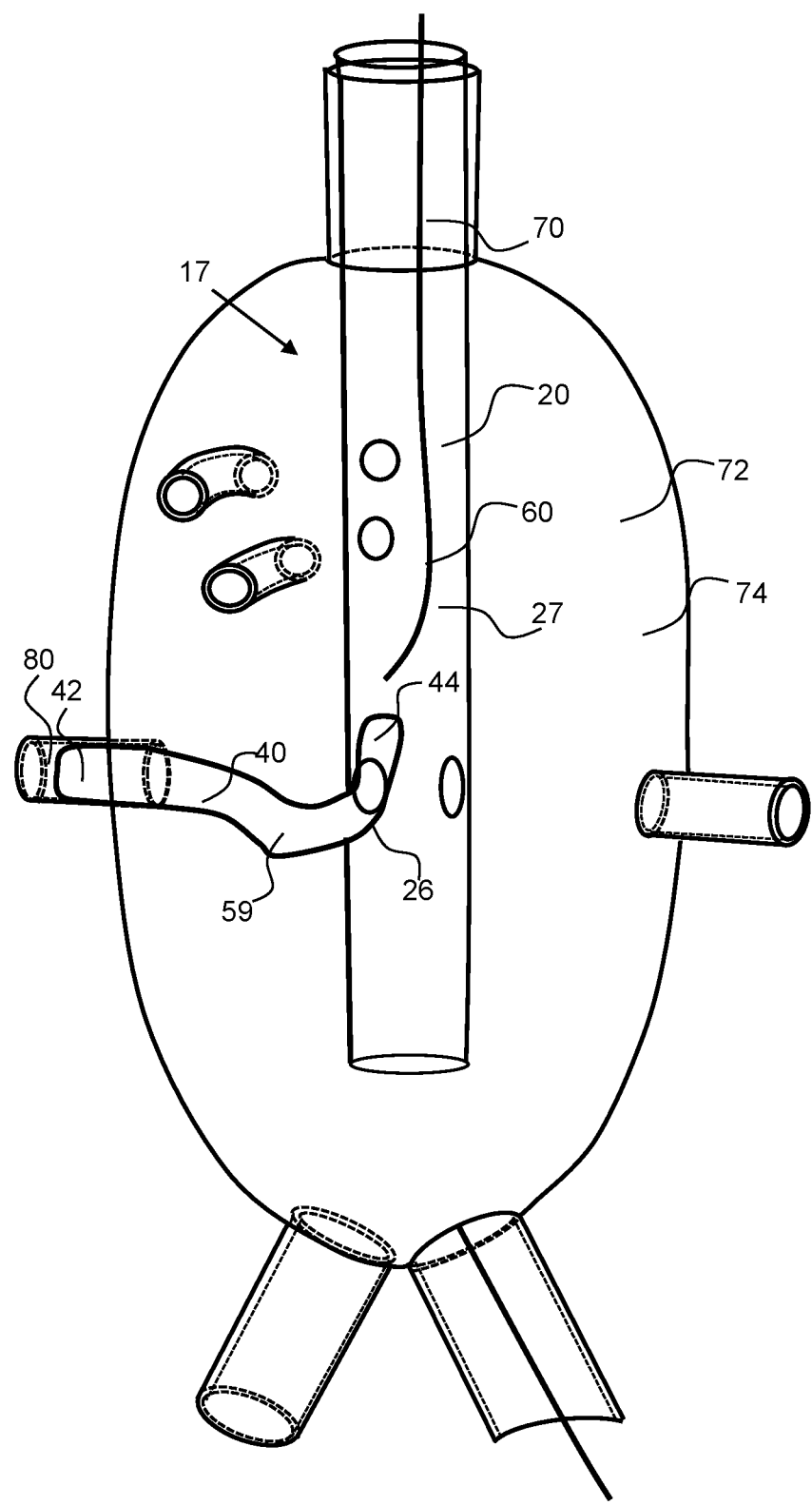
FIG. 25 shows the graft of FIG. 24, with the second end being deployed by the withdraw of the serpentine ripcord, wherein the branch graft deploys from the second end toward the first end.

Referring now to FIGS. 23 to 25, a branch graft 40 has a serpentine ripcord 60 that enables the branch graft to deploy in two or more sections. As shown in FIG. 23, the first end 42 of the branch graft 40 is configured within a branch vessel 80 and is at a constricted diameter 50 or has a constricted portion an offset distance 82 from the first end 42. The first deployed portion 54 is within a center portion of the branch graft 40, or between the first end 42 and second end 44, with both the first and second ends 42, 44 constricted to a constricted diameter 50. The first deployed portion 54 determines the length of the branch graft 40 from the first end 42 that will fit into the branch vessel 80. As shown in FIG. 24, the first end 42 of the branch graft 40 has been deployed, the second deployed portion 57, by pulling and withdrawing a length of the serpentine ripcord 60 and the second end 44 of the branch graft 40 is moved into the conduit 27 of the main graft 20 through the main graft aperture 26. As shown in FIG. 25, the serpentine ripcord 60 has been pulled completely from the branch graft 40 to deploy the third section, or third deployed portion 59, of the branch graft 40, the portion from the second end 44 to the first deployed portion 54, to completely deploy branch graft 40 to create a connection conduit from the main graft conduit 27 to the branch vessel 80.

Figures 26, 27:
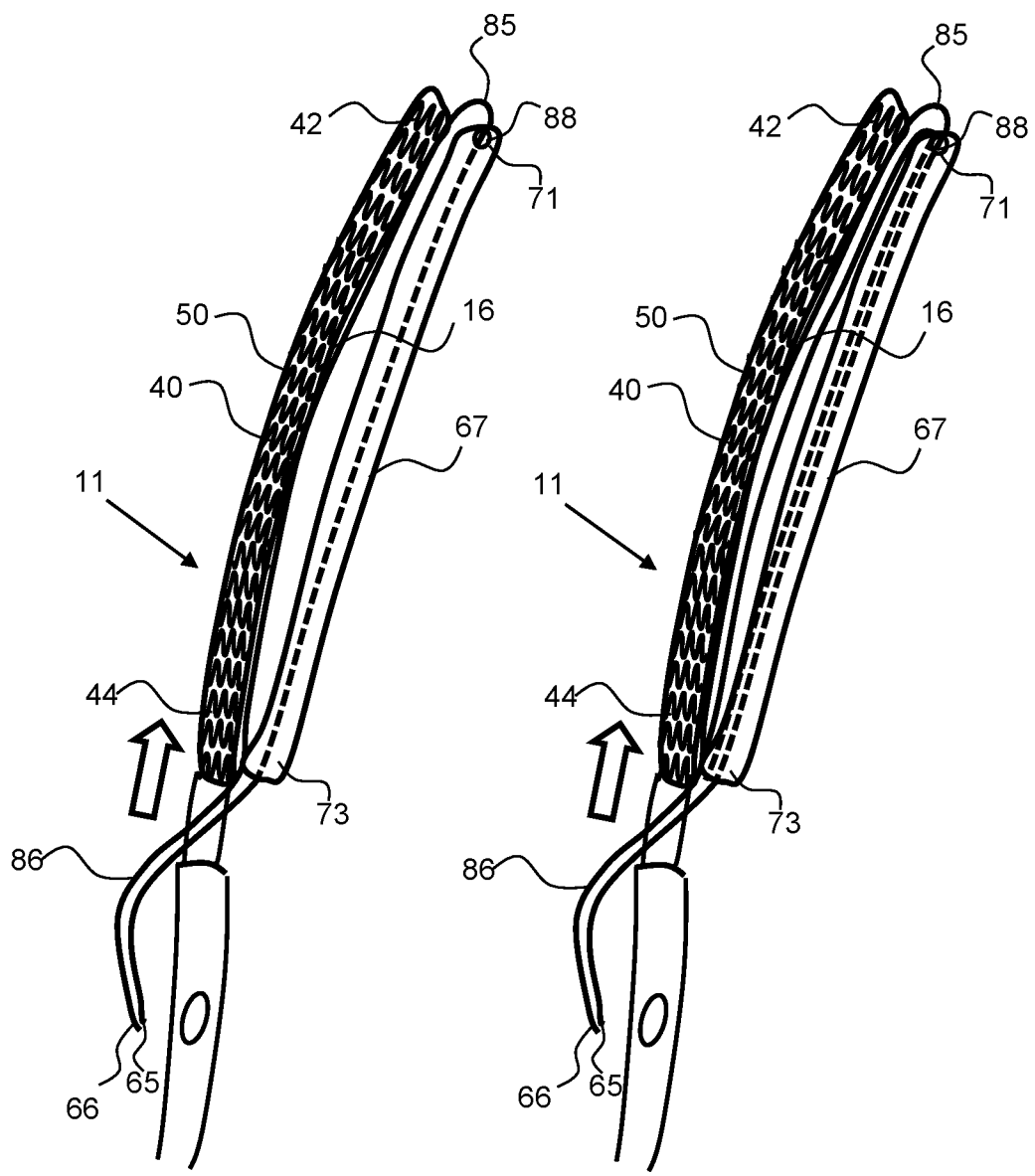
FIG. 26 shows an exemplary stent graft 11 with a locating sheath configured along the length of the stent graft and having an end of a ripcord extending through the sheath.
FIG. 27 shows an exemplary stent graft 11 with a locating sheath configured along the length of the stent graft and having both ends of a ripcord extending through the sheath.

As shown in FIG. 26, a first end extension 85 of a ripcord 16 extends through an attachment feature 88, an aperture in a locating sheath 67, in this embodiment. The first end extension 85 is an extension of the ripcord 16 from the first end 42 of the branch graft 40. A second end extension 86, extending from the second end 44 of the branch graft 40, extends directly out of the body. The locating sheath 67 has a first end 71 and a second end 73. The locating sheath 67 may be used to locate the second end 44 of the branch graft 40 into a second conduit. The ripcord 16 is coupled to the branch graft 40 to deploy the branch graft 40 and has two ends, a first end 65 and a second end 66. When the first end 65, or first end extension 85 is pulled, the branch graft 40 deploys from the first end 42 to toward the second end 44. The first end 71 of the locating sheath 67 will move along the length of the branch graft 40 as it is deployed from the first end 42 to the second end 44, when the first end extension 85 is pulled. The locating sheath 67 can be used to position the second end 44 of the branch graft 40 into a second conduit. The first end 71 of the locating sheath 67 may be configured proximal the second end 44 of the branch graft 40, and the first end 71 of the locating sheath 67 may be moved into a second conduit, thereby moving the second end 44 of the branch graft 40 into said second conduit. When the second end 44 of the branch graft 40 is located in the second conduit, further pulling of the first end extension 85 or the second end extension 86 will deploy the remaining portion of the branch graft 40. Pulling of the second end extension 86 of the ripcord 16 would deploy the branch graft 40 from the second end 44 to toward the first end 42 and pulling of the first end extension 85 would deploy the branch graft 40 from the first deployed portion 54 toward the second end 44.

As shown in FIG. 27, a loop is formed by the ripcord 16 with an end of the loop proximal to the second end 44. Both the first end extension 85 and the second end extension 86 extend through the locating sheath 67. One of the end extensions 85, 86 may extend through an aperture 88 in the locating sheath 67. Again, pulling and withdrawing the first end extension 85 will result in deployment of the graft 40 from the first end 42 to the second end 44 to produce a first deployed portion 54. The first end 71 of the sheath 67 may then be used to located the second end 44 of the branch graft 40 in a second conduit. Again, the remaining constricted portion of the branch graft 40 can be deployed by withdraw of either the first or second end extensions 85,86. When the first end 65 of the ripcord 16 is pulled, the branch graft 40 will deploy from the first end 42 toward the second end 44 and when the second end 66 of the ripcord 16 is pulled the branch graft 40 will deploy from the second end 44 toward the first end 42.

Figure 28:
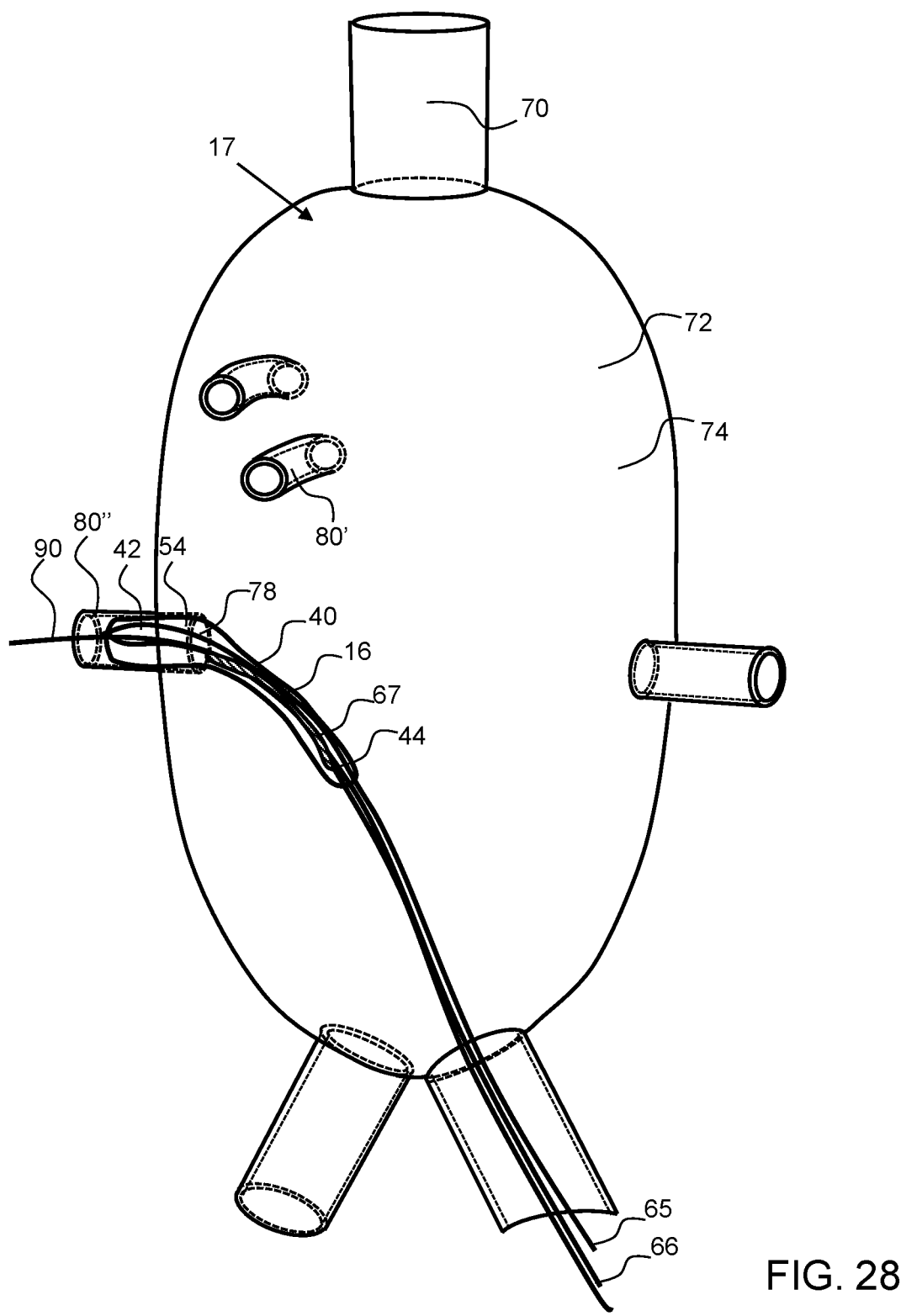
FIG. 28 shows an exemplary branch graft configured in a branch vessel with a locating sheath configured thereon along a portion of the length of the branch graft.
Figure 29:
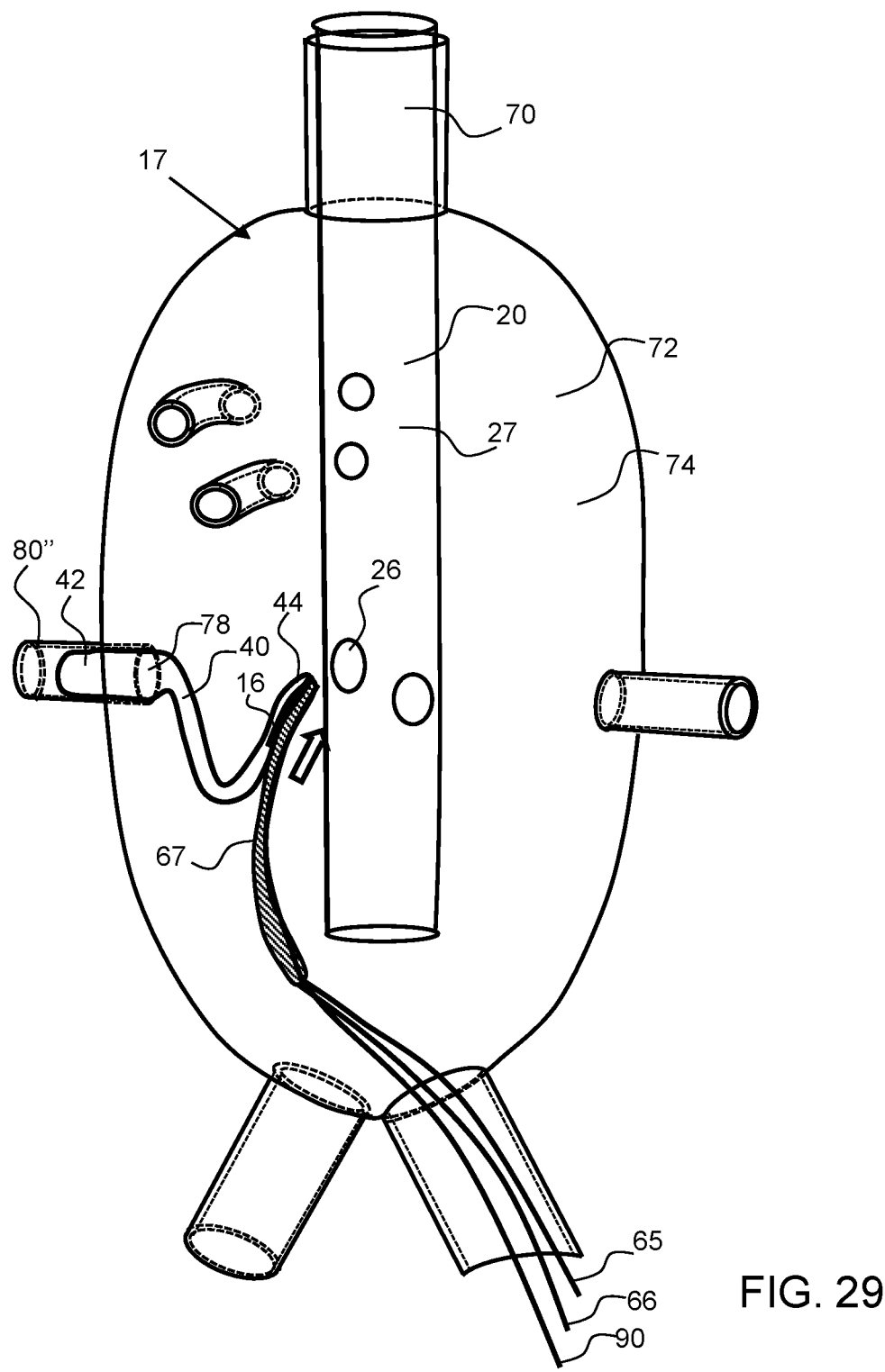
FIG. 29 shows the exemplary branch graft of FIG. 28, with the first end retained in the branch graft and the second end coupled with the locating sheath by a ripcord extension from the branch graft.
Figure 30:
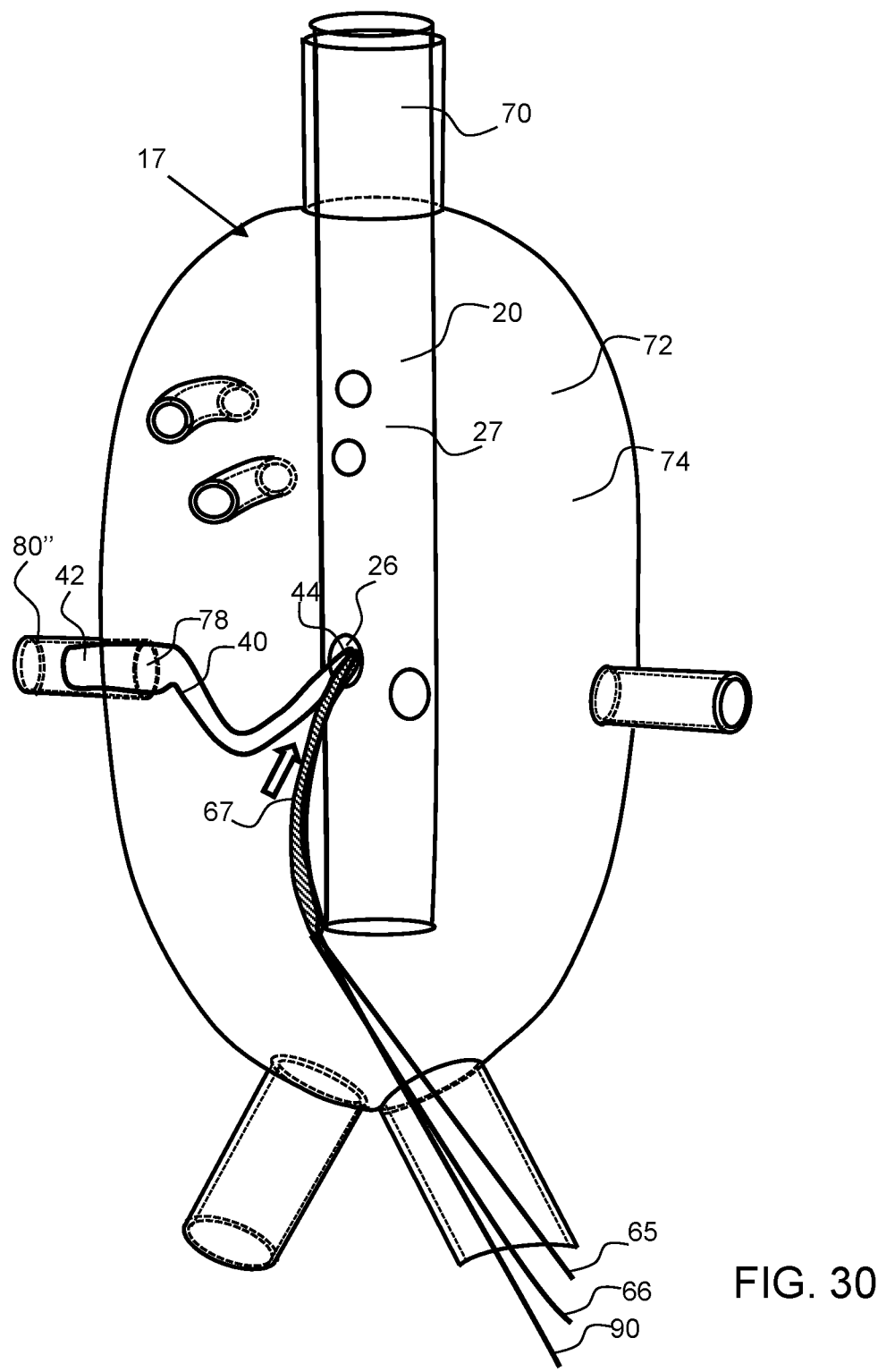
FIG. 30 shows the exemplary branch graft of FIG. 29, with the locating sheath moving the second end of the branch graft into the conduit of the main graft 20.

Referring now to FIGS. 28 to 30, a branch graft 40 is located into a second conduit 27 with the use of a locating sheath 67. As shown in FIG. 28, a branch graft 40 with a locating sheath 67 is located in a vessel 70 with the first end 42 located in a branch vessel 80". The first end 65 of the ripcord 16 has been withdrawn to deploy a portion of the branch graft 40 from the first end 42 to create a first deployed portion 54 and to retain the branch graft 40 in the branch vessel 80". The locating sheath 67 is connected to the branch graft 40 proximal the second end 44. As shown in FIG. 29, the locating sheath 67 is being used to position and move the second end 44 of the branch graft 40 into the conduit 27 of the main graft 20, through the main graft aperture 26. The ripcord 16 can further be withdrawn to deploy the remaining portion of the branch graft 40 to create a branching conduit from the conduit 27 of the main graft 20 to the conduit of the branch vessel 80. FIG. 29 shows the exemplary branch graft 40 of FIG. 28, with the first end 42 retained in the branch vessel 80" and the second end 44 being directed by the locating sheath 67 toward the aperture 26. FIG. 30 shows the exemplary branch graft 40 of FIG. 29, with the locating sheath 67 positioning the second end 44 of the branch graft 40 through the aperture 26 and into the conduit 27 of the main graft 20.

It will be apparent to those skilled in the art that various modifications, combinations and variations can be made in the present invention without departing from the spirit or scope of the invention. Specific embodiments, features and elements described herein may be modified, and/or combined in any suitable manner. Thus, it is intended that the present invention cover the modifications, combinations and variations of this invention provided they come within the scope of the appended claims and their equivalents.

What is claimed is:

1. A method of locating and securing a branch graft in two separate conduits comprising:

configuring a first end of a branch graft into an opening of a first conduit a first insertion length so that a second end of the branch graft extends from said first conduit opening, the first end being constricted to a first constricted diameter;

pulling a ripcord to deploy the first end of the branch graft within the first conduit from the first constricted diameter so that the first end of the branch graft deploys a first deployed distance;

pushing on a locating sheath to position a portion of the locating sheath and the second end of the branch graft into a second conduit, the second end being constricted to a second constricted diameter, and a portion of a length of the ripcord extending through the locating sheath;

pulling on a first end and a second end of the ripcord to remove the locating sheath and to deploy the second end of the branch graft from the second constricted diameter so that the second end of the branch graft is deployed from the second end of the branch graft toward the first end of the branch graft; and expanding the branch graft to a deployed state, wherein the branch graft is expanded toward said expanded diameter along the length of the branch graft, the branch graft retained within the first conduit and within the second conduit so that the branch graft couples the first conduit with the second conduit.

2. The method of claim 1, wherein the branch graft is a stent graft.

3. The method of claim 1, wherein the branch graft is a self-expanding stent graft.

4. The method of claim 1, wherein the ripcord extends from a location proximal the first end toward the second end and then back toward the first end.

5. The method of claim 1, wherein the first insertion length is defined by a first deployed portion of the branch graft starting an offset distance from the first end.

6. The method of claim 1, wherein the ripcord has a serpentine configuration.

7. A method of locating and securing a branch graft in two separate conduits comprising:

configuring a first end of a branch graft into an opening of a first conduit a first insertion length so that a second end of the branch graft extends from said first conduit opening, the first end being constricted to a first constricted diameter;

pulling a ripcord to deploy the first end of the branch graft within the first conduit from the first constricted diameter so that the first insertion length is defined by a first deployed portion of the branch graft starting an offset distance from the first end;

pushing on a locating sheath to position a portion of the locating sheath and the second end of the branch graft into a second conduit, the second end being constricted to a second constricted diameter, and a portion of a length of the ripcord extending through the locating sheath;

pulling on a first end and a second end of the ripcord to remove the locating sheath; and expanding the branch graft to a deployed state, wherein the branch graft is expanded toward said expanded diameter and is retained within the first conduit and within the second conduit so that the branch graft couples the first conduit with the second conduit.

8. The method of claim 7, wherein the ripcord has a serpentine configuration, and wherein when the ripcord deploys the first end of the branch graft within the first conduit, the first end of the branch graft deploys a first deployed distance, and wherein subsequent pulling of the ripcord deploys the second end of the branch graft from the second constricted diameter to completely deploy the branch graft along the length of the branch graft.

9. The method of claim 8, wherein the subsequent pulling of the ripcord deploys the second end of the branch graft from the second end of the branch graft toward the first end of the branch graft.

10. The method of claim 9, wherein the ripcord extends from a location proximal the first end toward the second end and then back toward the first end.

11. The method of claim 7, wherein the branch graft is a stent graft.

12. The method of claim 7, wherein the branch graft is a self-expanding stent graft.

* * * * *